(12) United States Patent
Brown

(10) Patent No.: US 6,662,116 B2
(45) Date of Patent: Dec. 9, 2003

(54) METHOD FOR ANALYZING AN UNKNOWN MATERIAL AS A BLEND OF KNOWN MATERIALS CALCULATED SO AS TO MATCH CERTAIN ANALYTICAL DATA AND PREDICTING PROPERTIES OF THE UNKNOWN BASED ON THE CALCULATED BLEND

(75) Inventor: James M. Brown, Flemington, NJ (US)

(73) Assignee: ExxonMobile Research and Engineering Company, Annandale, NJ (US)

( * ) Notice: Subject to any disclaimer, the term of this patent is extended or adjusted under 35 U.S.C. 154(b) by 126 days.

(21) Appl. No.: 10/023,031

(22) Filed: Nov. 30, 2001

(65) Prior Publication Data

US 2003/0195708 A1 Oct. 16, 2003

(51) Int. Cl.$^7$ ................................................ G01N 31/00
(52) U.S. Cl. .............................. 702/22; 702/27; 436/29
(58) Field of Search ........................ 702/27, 30, 22–26; 250/339.09, 339.12; 436/29, 60, 31–33; 703/2

(56) References Cited

U.S. PATENT DOCUMENTS

| | | | |
|---|---|---|---|
| 4,719,582 A | | 1/1988 | Ishida et al. ................. 364/498 |
| 5,119,315 A | * | 6/1992 | Kemp et al. ................... 702/27 |
| 5,121,337 A | | 6/1992 | Brown ......................... 364/498 |
| 5,218,529 A | * | 6/1993 | Meyer et al. .................. 702/28 |
| 5,301,125 A | | 4/1994 | Chimenti et al. ............ 364/498 |
| 5,360,972 A | * | 11/1994 | DiFoggio et al. ....... 250/339.12 |
| 5,412,581 A | * | 5/1995 | Tackett ......................... 702/30 |
| 5,424,951 A | * | 6/1995 | Nobe et al. .................. 701/200 |
| 5,446,681 A | * | 8/1995 | Gethner et al. ............... 702/27 |
| 5,699,269 A | | 12/1997 | Ashe et al. .................. 364/499 |
| 5,699,270 A | | 12/1997 | Ashe et al. .................. 364/500 |
| 6,070,128 A | | 5/2000 | Descales et al. .............. 702/30 |
| 6,275,775 B1 | | 8/2001 | Baco et al. ................... 702/25 |

* cited by examiner

*Primary Examiner*—Kamini Shah
(74) *Attorney, Agent, or Firm*—Ronald D. Hantman

(57) ABSTRACT

A method for determining a property of an unknown material including the steps of determining the IR spectrum of the unknown material, fitting the IR spectrum to a linear combination of known spectra in a database, wherein a database includes spectra of reference materials whose assay properties are known, and determining the property of the unknown material from the assay properties of the reference materials.

72 Claims, 10 Drawing Sheets

Fig. 2

METHOD FOR ANALYZING AN UNKNOWN MATERIAL AS A BLEND OF KNOWN MATERIALS CALCULATED SO AS TO MATCH CERTAIN ANALYTICAL DATA AND PREDICTING PROPERTIES OF THE UNKNOWN BASED ON THE CALCULATED BLEND

BACKGROUND OF THE INVENTION

The present invention is a method for analyzing an unknown material using a multivariate analytical technique such as spectroscopy, or a combination of a multivariate analytical technique and inspections. Such inspections are physical or chemical property measurements that can be made cheaply and easily on the bulk material, and include but are not limited to API or specific gravity and viscosity. The unknown material is analyzed by comparing its multivariate analytical data (e.g. spectrum) or its multivariate analytical data and inspections to a database containing multivariate analytical data or multivariate analytical data and inspection data for reference materials of the same type. The comparison is done so as to calculate a blend of a subset of the reference materials that matches the containing multivariate analytical data or containing multivariate analytical data and inspections of the unknown. The calculated blend of the reference materials is then used to predict additional chemical, physical or performance properties of the unknown using measured chemical, physical and performance properties of the reference materials and known blending relationships.

Within the petrochemical industry, there are many instances where a very detailed analyses of a process feed or product is needed for the purpose of making business decisions, planning, controlling and optimizing operations, and certifying products. Herein below, such a detailed analysis will be referred to as an assay, a crude assay being one example thereof. The methodology used in the detailed analysis may be costly and time consuming to perform, and may not be amenable to real time analysis. It is desirable to have a surrogate methodology that can provide the information of the detailed analysis inexpensively and in a timely fashion. The present invention is one such surrogate methodology.

Infrared spectroscopy, and in particular near-infrared spectroscopy, is widely used for the quantitative analysis of petrochemicals. For most applications, linear regression models are developed that relate the measured spectrum to the chemical, physical and performance properties of the material. Chemical properties include but are not limited to elemental and molecular compositions. Physical properties include but are not limited to density, viscosity, and cold flow properties such as pour, cloud or freeze point. Performance properties include but are not limited to octane and cetane numbers. While such linear regression models have been successfully used for many petrochemical applications, they are of limited utility for the detailed analysis of process feeds and products. The detailed analysis (assay) may involve hundreds of chemical, physical and performance parameters, thereby requiring the development and maintenance of an unmanageably large number of regression models. Further, many of the properties of interest may be complex, nonlinear functions of composition that are not readily predicted using linear regression models. Finally, the detailed analysis (assay) may include composition and property data for subfractions of the whole sample that are not readily predicted using linear regression models based on spectra of the whole sample. The current invention avoids these limitations by using a novel algorithmic approach to represent an unknown material as a blend of known reference materials. The current invention can readily predict large numbers of chemical, physical and performance properties of a material, can predict nonlinear properties providing nonlinear blending rules are known, and can predict chemical, physical and performance properties of subfractions of a material providing such properties were measured on similar subfractions of the reference materials and providing that blending relationships for the properties are known.

Alternative approaches that do not involve linear regression have been applied to spectroscopic data in an attempt to predict chemical, physical and performance properties of petrochemicals. For example, non-linear post-processing methods and neural networks have been employed to improve predictions for properties that are nonlinear functions of composition. Application of these analyses might address non-linearity, but they would only add to the complexity of the unmanageably large number of models needed for prediction of the detailed analysis (assay). Topology based approaches have been applied to spectral data so as to identify reference materials that are sufficiently similar to the material being analyzed to allow properties to be inferred. However, the topology approach requires a much denser database than the current invention to ensure that there are sufficiently similar references to any sample being analyzed. For detailed analyses (assays), the cost of producing a sufficiently dense database to utilize the topological approach is prohibitive. None of the alternative approaches have been shown to be reliably capable of predicting properties of sub-fractions of a sample based on spectra of the whole sample.

While the preferred embodiment of the present invention utilizes extended mid-infrared spectroscopy (7000–400 $cm^{-1}$), similar results could potentially be obtained using other multivariate analytical techniques. Such multivariate analytical techniques include other forms of spectroscopy including but not limited to near-infrared spectroscopy (12500–7000 $cm^{-1}$), UV/visible spectroscopy (200–800 nm), fluorescence and NMR spectroscopy. Similar analyses could also potentially be done using data derived multivariate analytical techniques such as simulated gas chromatographic distillation (GCD) and mass spectrometry or from combined multivariate analytical techniques such as GC/MS. In this context, the use of the word spectra herein below includes any vector or array of analytical data generated by a multivariate analytical measurement such as spectroscopy, chromatography or spectrometry or their combinations.

The present invention is applicable to the prediction of chemical, physical and performance properties of crude oils. Both properties of whole crude, and of any distillate cut of the crude can be predicted. The present invention is also applicable to petrochemical process and product streams. The reference materials used in the analysis and the unknowns that are analyzed can be process feeds, products or both. For example, the reference materials can be gas oil feeds to a catalytic cracking unit for which detailed molecular composition analyses have been performed. The present invention can be used to predict the molecular compositions of unknown gas oils. The present invention is also applicable to the prediction of extraction response data for waxy distillate feeds to lube extraction and dewaxing processes. The extraction response data includes but is not limited to raffinate and dewaxed raffinate yield, raffinate and dewaxed raffinate viscosity and viscosity index, raffinate and dewaxed raffinate saturates content, and raffinate and dewaxed raffinate refractive index as a function of extraction and dewaxing conditions. The reference materials are waxy distillate feed samples for which extraction and dewaxing data was measured. The present invention is used to predict extraction and dewaxing data for unknown waxy distillate feeds.

In the petrochemical industry, extremely detailed analyses of feed and product materials (assays) are often utilized for making business decisions, for planning, controlling and optimizing operations, and for certifying products. Chief among these analyses is the crude assay. When a crude oil is assayed, it is distilled in two steps. A method such as ASTM D2892 (see. Annual Book of ASTM Standards, Volumes 5.01–5.03, American Society for Testing and Materials, Philadelphia, Pa.) is used to isolate distillate cuts boiling below approximately 650° F. (343° C.). The residue from this distillation is further distilled using a method such as ASTM D5236 to produce distillate cuts covering the range from 650° F. to approximately 1000–1054° F. (343° C. to 538–568° C.) and a vacuum residue cut. At a minimum, cuts corresponding to typical products or unit feeds are typically isolated, including LPG (Initial Boiling Point to 68° F.), LSR (68–155° F.), naphtha (155–350° F.), kerosene (350–500° F.), diesel (500–650° F.), vacuum gas oil (650° F. to 1000–1054° F.), and vacuum residue (1000–1054° F.+). Each distillate cut is then analyzed for elemental, molecular, physical and/or performance properties. The specific analyses conducted depend on the typical disposition of the cut. Example analyses are shown in Table 1. The data derived from these analyses will typically be stored is in an electronic database where it can be mathematically manipulated to estimate crude qualities for any desired distillation range. For example, commercial crude assay libraries are available from Haverly Systems Inc., and HPI Consultants Inc., both of which provide tools for manipulating the data, as does Aspentech Inc. Assay data is published by Crude Quality Inc., by Shell Oil Company, and by Statoil. The property versus distillation temperature data is typically fit to smooth curves that can then be used to estimate the property for any desired distillation cut.

TABLE 1

| Distillate Cut | Possible Analyses | Method |
|---|---|---|
| Whole Crude | API Gravity, Specific Gravity and/or density | ASTM D287, D4052, D5002 |
| | Fe, V, Ni, Na | ICP-AES |
| | Nitrogen | ASTM D4629 |
| | Basic Nitrogen | UOP 269 |
| | Sulfur | ASTM D2622, D4294, or D5453 |
| | Mercaptan Sulfur and H$_2$S | ASTM D3227 |
| | Volume % and Weight % Yields | ASTM D2892 and D5236 |
| | Simulated Distillation | ASTM D5307 |
| | Neutralization Number | ASTM D664 |
| | Pour Point | ASTM D97, D5853 or D5950 |
| | Reid Vapor Pressure | ASTM D323 |
| | Sediment and Water | ASTM D 1796 |
| | Viscosity | ASTM D445 |
| LPG (Initial Boiling Point to 68° F.) | API Gravity, Specific Gravity and/or density | ASTM D287, D1298, D4052, D5002 |
| | Sulfur | ASTM D2784, D3246 |
| | Mercaptan Sulfur and H$_2$S | ASTM D3227 |
| | n-paraffins, i-paraffins, naphthenes, aromatics | Gas Chromatography |
| | Reid Vapor Pressure | ASTM D323 |
| | Research and Motor Octane | ASTM D2699 and D2700 |
| LSR (68–155° F.) | API Gravity, Specific Gravity and/or density | ASTM D287, D1298, D4052, D5002 |
| | Sulfur | ASTM D3120, D5453 |
| | Nitrogen | ASTM D4629 |
| | Mercaptan Sulfur and H$_2$S | ASTM D3227 |
| | n-paraffins, i-paraffins, naphthenes, aromatics | Gas Chromatography |
| | benzene | Gas Chromatography |
| | Reid Vapor Pressure | ASTM D323 |
| | Research and Motor Octane | ASTM D2699 and D2700 |
| Naphtha (155–35° F.) | API Gravity, Specific Gravity and/or density | ASTM D287, D1298, D4052, D5002 |
| | Sulfur | ASTM D2622, D4294, or D5453 |
| | Nitrogen | ASTM D4629 |
| | Mercaptan Sulfur | ASTM D3227 |
| | n-paraffins, i-paraffins, naphthenes, aromatics | Gas Chromatography |
| | aromatic ring distribution | HPLC |
| | benzene | Gas Chromatography |
| | naphthelenes | ASTM D1840 |
| | Neutralization Number | ASTM D664 |
| | Reid Vapor Pressure | ASTM D323 |
| | Research and Motor Octane | ASTM D2699 and D2700 |
| | Viscosity | ASTM D445 |
| | Flash Point | ASTM D93 |

TABLE 1-continued

| Distillate Cut | Possible Analyses | Method |
| --- | --- | --- |
| Kerosene (350–500° F.) | API Gravity, Specific Gravity and/or density | ASTM D287, D1298, D4052, D5002 |
| | Sulfur | ASTM D2622, D4294, or D5453 |
| | Nitrogen | ASTM D4629 |
| | Mercaptan Sulfur | ASTM D3227 |
| | aromatic ring distribution | HPLC |
| | hydrocarbon types | ASTM D1319 |
| | naphthelenes | ASTM D1840 |
| | Neutralization Number | ASTM D664 |
| | Viscosity | ASTM D445 |
| | Smoke Point | ASTM D1322 |
| | Freeze Point | ASTM D2386 |
| | Cloud Point | ASTM D2500, D5772 |
| | Pour Point | ASTM D97 |
| | Cold Filter Plugging Point | IPO 309 |
| | Cetane Index | ASTM D976, D4737 |
| | Cetane Number | ASTM D613 |
| Diesel (500–650° F.) | API Gravity, Specific Gravity and/or density | ASTM D287, D1298, D4052, D5002 |
| | Sulfur | ASTM D2622, D4294, or D5453 |
| | Nitrogen | ASTM D4629 |
| | Mercaptan Sulfur | ASTM D3227 |
| | aromatic ring distribution | HPLC |
| | hydrocarbon types | ASTM D1319 |
| | Neutralization Number | ASTM D664 |
| | Viscosity | ASTM D445 |
| | Freeze Point | ASTM D2386 |
| | Cloud Point | ASTM D2500, D5772 |
| | Pour Point | ASTM D97 |
| | Cold Filter Plugging Point | IPO 309 |
| | Cetane Index | ASTM D976, D4737 |
| | Cetane Number | ASTM D613 |
| Vacuum Gas Oil (650° F. to 1000–1054° F.) | API Gravity, Specific Gravity and/or density | ASTM D287, D1298, D4052, D5002 |
| | Sulfur | ASTM D2622, D4294, or D5453 |
| | Nitrogen | ASTM D4629 |
| | aromatic ring distribution | HPLC |
| | Neutralization Number | ASTM D664 |
| | Viscosity | ASTM D445 |
| | Pour Point | ASTM D97 |
| | Carbon Residue | ASTM D189 or D4530 |
| | V, Ni | ICP-AES |
| Vacuum Residue (1000–1054° +). | API Gravity, Specific Gravity and/or density | ASTM D287, D1298, D4052, D5002 ASTM D2622, D4294, or D5453 |
| | Sulfur | |
| | Nitrogen | ASTM D4629 |
| | aromatic ring distribution | HPLC |
| | Neutralization Number | ASTM D664 |
| | Viscosity | ASTM D445 |
| | Pour Point | ASTM D97 |
| | Carbon Residue | ASTM D189 or D4530 |
| | V, Ni | ICP-AES |
| | Penetration | ASTM D1321 |

Depending on the intended use of the assay data, different organizations will employ different assay strategies. If more distillate cuts are taken covering smaller temperature ranges, the accuracy of the property versus temperature curves is improved. However, the volume of oil that needs to be distilled to provide adequate samples for reference analyses is increased, as is the number of required analyses. Thus, the cost and completion time of the assay is increased. For compositional and process modeling, extremely detailed analyses may be employed, as for example the HDHA method described by Jacob, Quann, Sanchez and Wells (*Oil and Gas Journal*, Jul. 6, 1998).

A detailed crude assay can take several weeks to months to complete. As a result, the assay data used for making business decisions, and for planning, controlling and optimizing operations is seldom from the cargoes currently being bought, sold or processed, but rather historical data for "representative" past cargoes. The assays do not account for variations between cargoes that can have a significant effect on operations. K. G. Waguespack (*Hydrocarbon Processing*, 77 (9), 1998 Feature Article) discusses the sources of oil quality variation, their effect on refinery operations, and the need for improved analytical technology for use in crude oil quality monitoring. Wagusepack lists sources of crude oil variability, both over time and during its transport life as: aging production reservoirs; changes in relative field production rates; mixing of crude in the gathering system; pipeline degradation vis-à-vis batch interfaces; contamination; and injection of significantly different quality streams into common specification crude streams. Such variations can cause significant changes in the value of the crude oil, and in the products that can be made from it.

Detailed analyses are conducted on many petrochemical feeds and products. R. J. Quann and S. B. Jaffe (*Ind. Eng. Chem. Res.* 1992, 31, 2483–2497) describe a Structured Oriented Lumping scheme for use in modeling petrochemical processes. The SOL scheme utilizes data collected via a combination of HPLC, field ionization mass spectrometry and gas chromatography/mass spectrometry (GC/MS) (Sullivan, R. F.; Bodluszynaski, M. M.; Fetzer, J. C.; *Energy Fuels* 1989, 3, 603–612). Jacob, et. al. (Jacob, S. M.; Quann, R. J.; Sanchez, E.; Wells, M. E.; *Oil and Gas Journal* 1998, 51–58) describe application of the SOL approach to various refining processes involved in lubricant manufacture. The analysis schemes used to generate the SOL data are complex and time consuming to apply. The current invention helps to maximize the utility of these SOL based process models for business decisions by providing a means of generating the SOL data rapidly, on minimal sample volumes.

Infrared and Raman spectroscopies have been employed for process analysis of a variety of petrochemical streams. G. M. Hieftje, D. E. Honigs and T. B. Hirschfeld (U.S. Pat. No. 4,800,279 Jan. 24, 1989) described the prediction of physical properties for simple hydrocarbon mixtures from near-infrared (NIR) spectra using multiple linear regression (MLR). D. A. Swinkels, P. M. Fredricks and P. R. Osborn applied FT-IR and Principal Components Regression (PCR) to the analysis of coals (U.S. Pat. No. 4,701,838 Oct. 20, 1987). J. M. Brown (U.S. Pat. No. 5,121,337 Jun. 9, 1992) describes a method for predicting property and composition data of samples using spectra and Constrained Principal Spectra Analysis (CPSA). R. Clarke describes a method for measuring properties of hydrocarbons using Raman spectroscopy (U.S. Pat. No. 5,139,334 Aug. 18, 1992). R. H. Clarke and D. Tang describe a method and mid-infrared apparatus for determining hydrocarbon fuel properties (U.S. Pat. No. 5,225,679 Jul. 6, 1993). D. C. Lambert and A. Martens (EP 2852521 and U.S. 5490085 Sep. 6, 1996) describe the prediction of octane number using NIR spectra and MLR, as does S. M. Maggard (U.S. Pat. No. 4,963,745 Oct. 16, 1990). Maggard also describes the estimation of paraffins, isoparaffins, aromatics, naphthenes and olefins in gasolines using NIR and MLR or Partial Least Squares (PLS) (U.S. Pat. No. 5,349,188 Sep. 20, 1994), the predicition of blend properties from the spectra of blend components using NIR and MLR (U.S. Pat. No. 5,223,714 Jun. 29, 193), and the prediction of oxygenates and oxygen content of gasolines using NIR spectra. S. Maggard and W. T. Welch discuss prediction of organic sulfur content for mid-distillate fuels using NIR spectra (U.S. Pat. No. 5,348,645 Sep. 20, 194). J. B. Cooper, M. B. Sumner; W. T. Welch and K. L Wise describe a method for measuring oxygen and oxygenate content of gasolines using Raman spectroscopy (U.S. Pat. No. 5,596,196 Feb. 21, 1997). R. R. Bledsoe, J. B. Cooper, M. B. Sumner; W. T. Welch, B. K. Wilt and K. L Wise describe a method of predicting octane number and Reid vapor pressure of gasolines using Raman spectroscopy (U.S. Pat. No. 5,892,228 Apr. 6, 1999). These methods typically involve linear models for individual properties, and are thus not necessarily useful for properties that are non-linear functions of composition, nor for prediction of properties of subfractions of the sample being analyzed. While they can provide rapid analyses on minimal sample volumes, their application for detailed analyses would require the development and maintenance of an impracticably large number of models. In addition, many of these NIR methods operate in spectral regions where crude oil is essentially opaque. Raman methods are typically not applicable to crude oils or other heavy hydrocarbons due to interferences from fluorescence. None of these methods employs a combination of infrared spectra and inspections.

A. Espinosa, A. Martens, G. Ventron, D. C. Lambert and A. Pasquier (EP 305090 and U.S. Pat. No. 5,475,612 Dec. 12, 1995) describe predicting physical properties of blends from near-infrared spectra of blend components using MLR. Products and ratios of absorbances were included in an attempt to predict nonlinear properties such as RON. A. Espinosa, D. C. Lambert, A. Martens and G. Ventron (EP 304232 and U.S. Pat. No. 5,452,232 Apr. 25, 1990) describe a method for predicting properties of process products from spectra of process feeds using NIR and MLR. Products and ratios of absorbances were again used to handle nonlinear properties. B. N. Perry and J. M. Brown describe a method for improving the prediction of nonlinear properties by post-processing results from linear models (U.S. Pat. No. 5,641,962 Jun. 24, 1997). J. M. Tolchard and A. Boyd (WO9417391) describe the use of NIR and neural networks for the prediction of hydrocarbon physical properties. While these methods could potentially be use to predict properties that have nonlinear relationships to composition, all would require that separate models be built for each property to be predicted. In addition, none of these methods uses spectra in combination with inspections.

R. DiFoggio, M. Sadhukhan and M. Ranc (U.S. Pat. No. 5,360,972 Nov. 1, 1994) describe a method for estimating physical properties of a material using a combination of infrared data and data indicative of trace level compounds. DiFoggio et. al. do not teach the use of infrared and inspection data, and their method would require separate models to be built for each property to be estimated.

B. Descales, D. Lambert, J. LLinas, A. Martens, S. Osta, M. Sanchez and S. Bages (U.S. Pat. No. 6,070,128 May 30, 2000) describe a topology based method for determining properties from NIR spectra. Their method calculates an Euclidean distance between the spectrum of the sample being analyzed and all of the reference spectra in the database. Reference samples whose spectra fall within a predetermined distance of the unknown spectra are selected, and the properties of the unknown are calculated as the average of the properties of the selected references. Alternatively, the spectrum of the unknown can be fit as a linear combination of the selected references, and the properties of the unknown calculated as the weighted combination of the reference sample properties. Nonlinear properties are handled through blending factors. If there are insufficient references within the predetermined distance of the unknown, the method provides a means of densifying the database to interpolate between the reference samples. While the method of Descales, et. al. can be used to analyze the unknown as if it were a blend of the reference samples, the blend components are limited to those samples who have spectra nearly identical to the spectrum of the unknown, i.e. the nearest neighbors in the spectral space. In addition, Descales, et. al. do not teach the combination of infrared and inspection data.

Other methodologies have been employed for detailed analyses of hydrocarbons. T. R. Ashe, R. W. Kapala and G. Roussis (U.S. Pat. No. 5,699,270 Dec. 16, 1997) employed PLS models of GC/MS data to predict chemical, performance, perceptual and physical properties of feed and product streams from various steps in lubricating oil manufacturing. T. R. Ashe, S. G. Roussis, J. W. Fedora, G. Felshy and W. P. Fitzgerald (U.S. Pat. No. 5,699,269 Dec. 16 ,1997) used PLS models of OGC/MS data to predict physical and chemical properties of crude oils. Both method employed separate models for each property predicted.

I. H. Cho, J. G. Choi and H. I. Chung (WO 00/39561) described an apparatus that combined a distillation unit and a spectrometer for analysis of crude oils. Separate chemometric models were employed for each property for each distillate cut.

K. Hidajat and S. M. Chong claim to measure total boiling point and density of crude oils from NIR spectra (*J. Near Infrared Spectroscopy* 8, 53–59 (2000)). Neither other whole crude properties, nor properties of distillate cuts were predicted.

SUMMARY OF THE INVENTION

The present invention is a method for determining a property of an unknown material. The invention includes the steps of determining the multivariate analytical data of the unknown material, fitting the multivariate analytical data to a linear combination of known multivariate analytical data in a database, wherein the database includes multivariate analytical data of reference materials whose assay properties are known, and determining the property of the unknown material from the assay properties of the reference materials.

In a preferred embodiment, the method includes the step of eliminating signals from the multivariate analytical data not relating to the molecular constituents. The step of eliminating signals may be performed by orthogonalizing the multivariate analytical data of the unknown and reference materials to examples of the signals to be eliminated.

In another preferred embodiment the method further includes the step of augmenting the multivariate analytical data with inspection data to form augmented data such that the augmented data of the unknown material is fit to a linear combination of multivariate analytical data augmented with inspection data of the known reference materials. The inspection data may be, but is not limited to, specific gravity or viscosity.

BRIEF DESCRIPTION OF THE DRAWINGS

FIG. 2 shows an example of polynomial corrections that might be employed to correct for baseline variations.

DETAILED DESCRIPTION OF THE PREFERRED EMBODIMENTS

Figure 1:
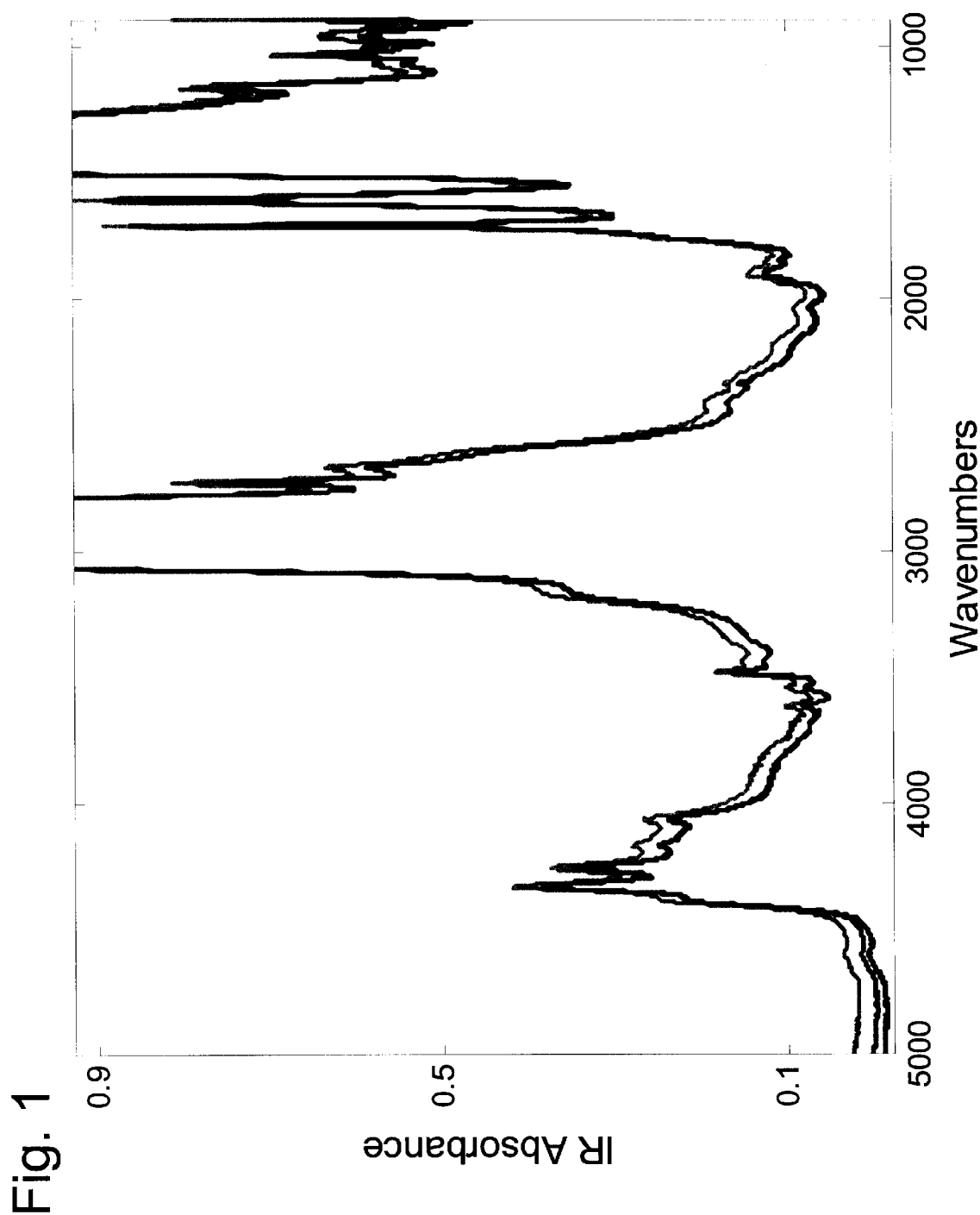
FIG. 1 shows an example of spectra of Orquida crude collected on three different spectrometers.

The present invention is a method of analyzing an unknown material such as a crude oil as if it were a blend of materials of known composition and properties. The invention utilizes a database containing multivariate analytical data such as spectra or multivariate analytical data and inspection data for reference materials whose composition and properties have previously been measured. The multivariate analytical data or multivariate analytical data and inspection data for the unknown material are fit as a linear combination of the multivariate analytical data or multivariate analytical data plus inspection data for the reference materials. The references so selected, and the proportions indicated by the fit are then used to calculate composition and property data for the unknown employing known blending relationships.

For crude oils, the present invention utilizes infrared data, preferably in the range from 7000 to 400 $cm^{-1}$, and most preferably in the range from 6000 to 900 $cm_{-1}$. Crude oil spectra are preferably collected at 65±1° C. using cells with a nominal pathlength of 0.2 mm. Portions of the preferred range in which the absorbance exceeds the linear response range of the instrument may be excluded from the data analysis. Similarly, portions of the preferred range that contain minimal information about the materials being analyzed, but which are subject to poor signal-to-noise or to interferences may be excluded from the data analysis. The data analysis methodology is not limited to data of this type or range. The same data analysis methodology could be applied to near-infrared, Raman, UV/visible or NMR spectra, or to GC or HPLC chromatograms.

The present invention operates in two modes. In a database development mode, multivariate analytical data such as spectra, inspections and detailed analyses (assays) are obtained on known materials, henceforth called reference materials. The multivariate analytical data are preprocessed using the method of Brown (U.S. Pat. No. 5,121,337) to remove various sources of variation that are not representative of the material being analyzed. The multivariate analytical data or the multivariate analytical data and inspections are combined in a database. In an analysis mode, the multivariate analytical data or the multivariate analytical data and inspections of an unknown material are obtained. The multivariate analytical data is preprocessed using the method of Brown, and then analyzed relative to this database in order to calculate a blend of the reference materials that most closely matches the multivariate analytical data or the multivariate analytical data and inspections of the unknown. The detailed analysis (assay) of the unknown is then predicted using the reference materials indicated by the blend and their proportions and known blending rules for the properties being predicted.

When spectral measurements are conducted on materials such as crude oils, the spectra collected can include a variety of signals that are not due solely to the organic components of the material. For example, FT-MIR spectra of crude oils may include absorbances due to water vapor and carbon dioxide in the spectrometer light path, absorbances due to water dispersed in the sample, baseline variations due to scattering and baseline variations due to instrument drift. If these extraneous signals are not corrected for, the blend calculated and the properties predicted may be in error.

Baseline variations are corrected for using the method of Brown (U.S. Pat. No. 5,121,337). Orthonormal polynomials are generated as examples of baseline variations. If the spectral data covers one continuous region, one set of polynomials are typically employed. If the spectral data is discontinuous due to exclusion of regions where the absorbance exceeds the linear response range of the instrument, separate sets of polynomials are preferably generated for each subregion. The polynomials are typically stored as column vectors that span the entire spectral range but are assigned a value of zero outside the range in which they were generated.

FIG. 1 shows an example of spectra of Orquidea crude collected on three different spectrometers. Differences in the instrumentation give rise to variations in the baseline among the spectra. If these differences are not compensated for, different blends would be calculated to match the three spectra, and different crude property predictions might be made.

Figure 2:
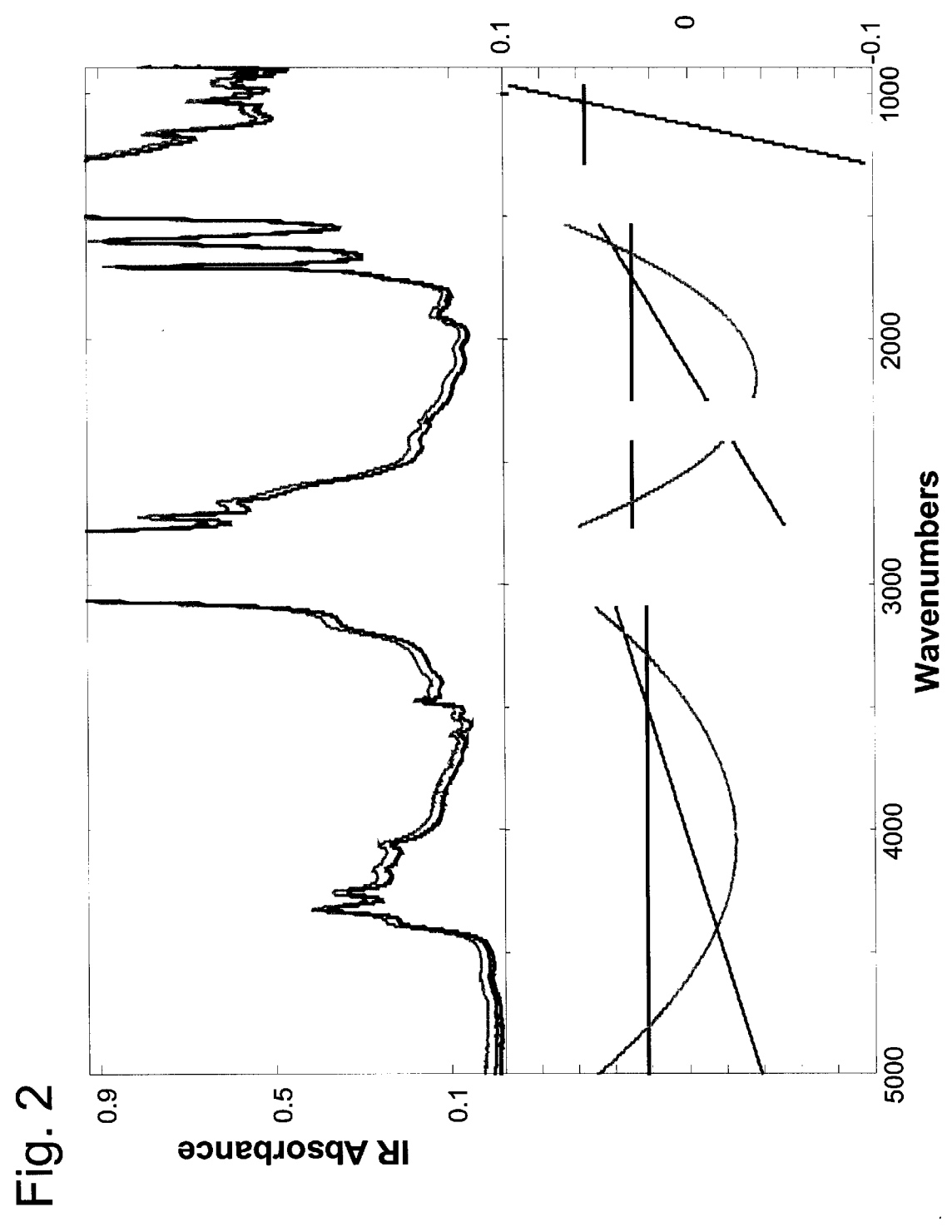

FIG. 2 shows an example of polynomial corrections that might be employed. The spectral data spans the range from 4999.6 to 969.1 cm$^{-1}$, the lower frequency limit being set by the cutoff in the CaF$_2$ cell window. Regions between 3096.2 and 2763.5 cm$^-$and between 1535.1 and 1281.5 cm$^{-1}$are excluded from the data to avoid absorbances that exceed 1.5. The region between 2421.2 and 2249.6 is excluded from the data analysis to avoid interferences due to carbon dioxide in the spectrometer light path. The excluded regions are indicated in the figure by the shaded rectangles. One set of orthogonal polynomials is generated to span the upper frequency range from 4999.6 to 3096.2 cm$^{-1}$. A second set of polynomials span the range from 2763.5 to 1535.1 cm$^{-1}$, being set to zero in the excluded range between 2421.2 and 2249.6 cm$^{-1}$. A third set of polynomials span the range from 1281.5 to 969.1 cm$^{-1}$. The maximum degree for each set of polynomials is set so as to correct for the typical baseline variations observed in that spectral range. The necessary degree of correction can be determined experimentally by collecting spectra of a representative material repetitively over an extended time period and determining the degrees of the polynomials needed to cancel the observed baseline variation. For this example, quadratic polynomials (degree 2) that include a constant, linear and quadratic term are used in the upper two frequency regions, and a linear (degree 1) polynomial (constant and linear term) is used in the lower frequency region.

Figure 3:
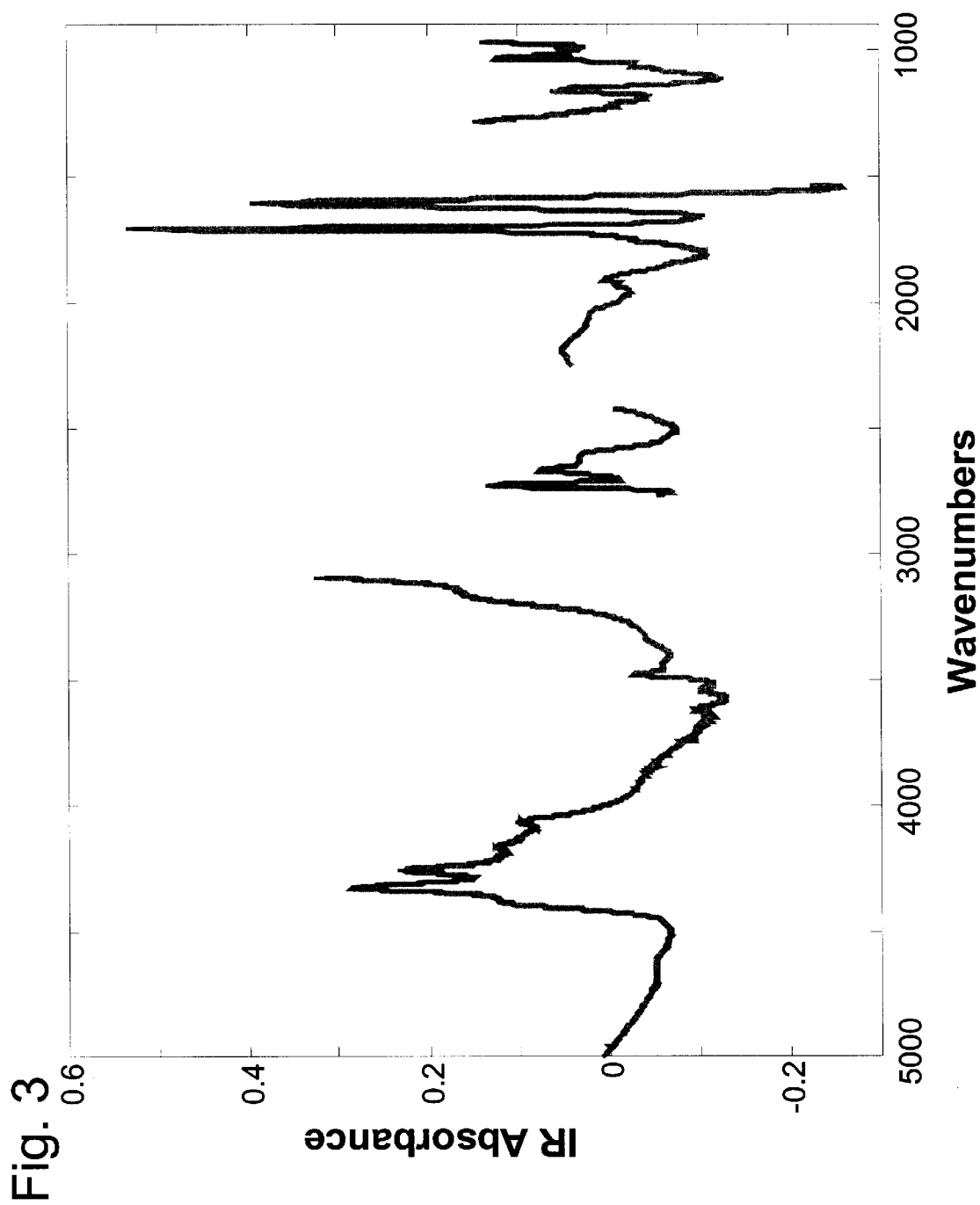
FIG. 3 shows the spectra of Orquida crude after orthogonalization to the polynomials.

FIG. 3 shows the same three crude spectra after orthogonalization to the polynomials. The baseline differences have been minimized such that the three spectra would yield essentially the same property predictions.

The baseline correction column vectors make up the columns of a matrix $U_p$. The matrix is of dimension f by p, where f is the number of spectral data points in the included spectral regions, and p is the total number of polynomial terms used in all the included regions.

Whereas baseline variations can typically be corrected for using calculated polynomials, other sources of variation are typically corrected for using experimentally derived data. For crude oils, absorbance and scattering due to dispersed water are often observed.

Figure 4:
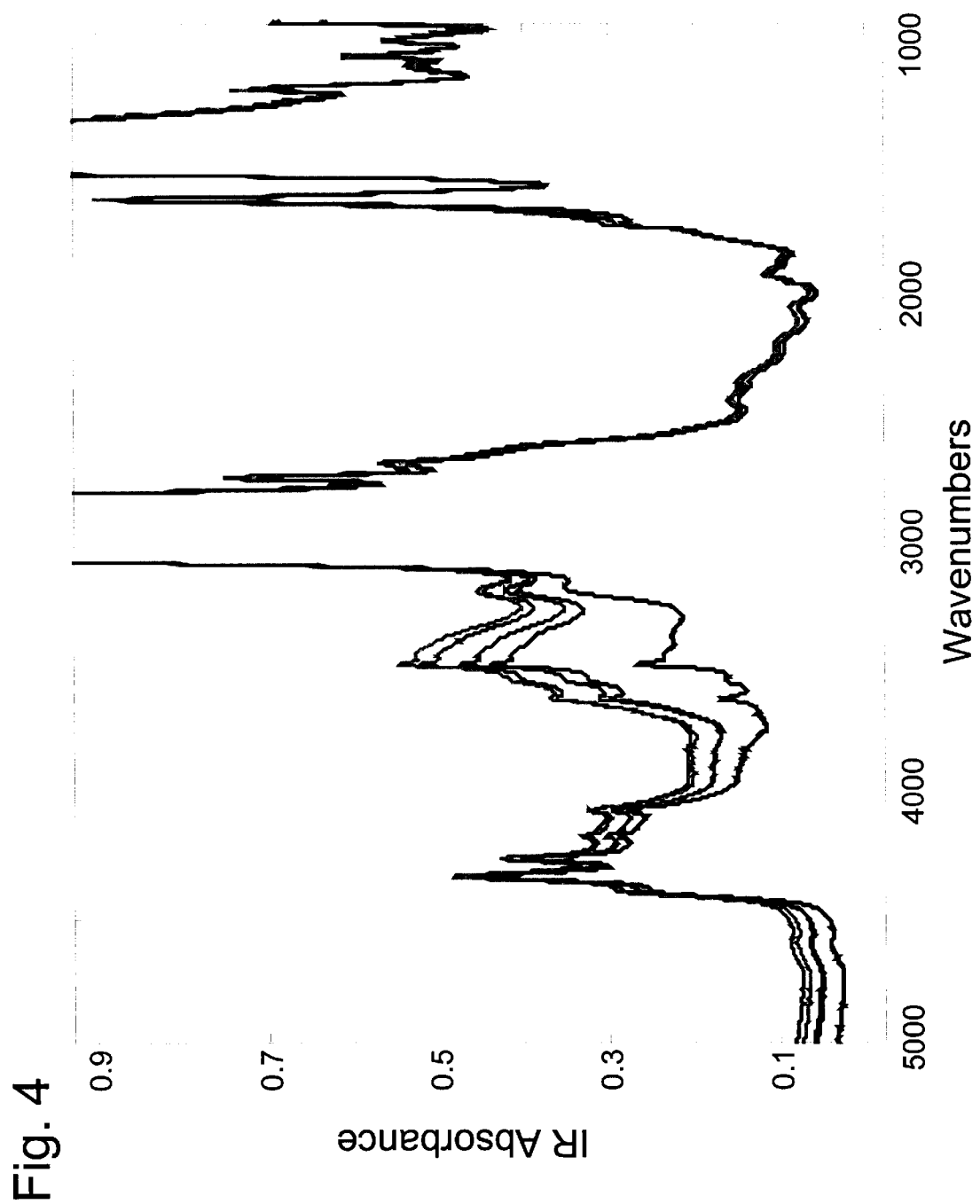
FIG. 4 shows 6 spectra of samples of Chocalho crude with various levels of dispersed water.

FIG. 4 shows 6 spectra of samples of a Chocalho crude with various levels of dispersed water. The water gives rise to a broad absorption in the range of 3400 cm$^{-1}$, a weaker absorption near 1630 cm$^{-1}$, and a baseline change due to scattering. If these variations are not corrected for, blend components can be selected based on a match to the water contamination as opposed to a match of the crude organic components, and incorrect property predictions may be made.

Figure 5:
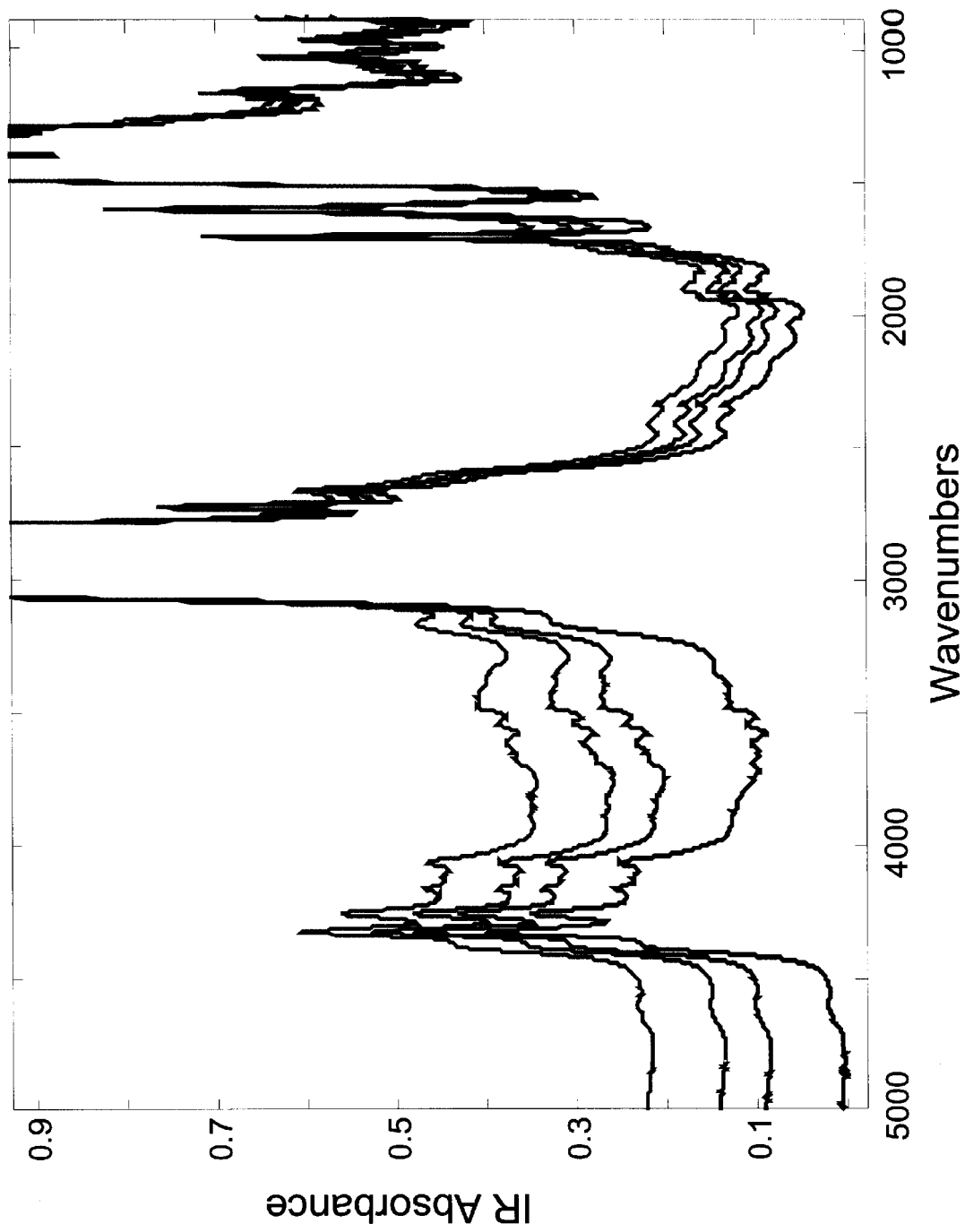
FIG. 5 shows spectra (from bottom to top) of Heidrun crude, and Heidrun crude that was treated with 1, 2 and 4% water
Figure 6:
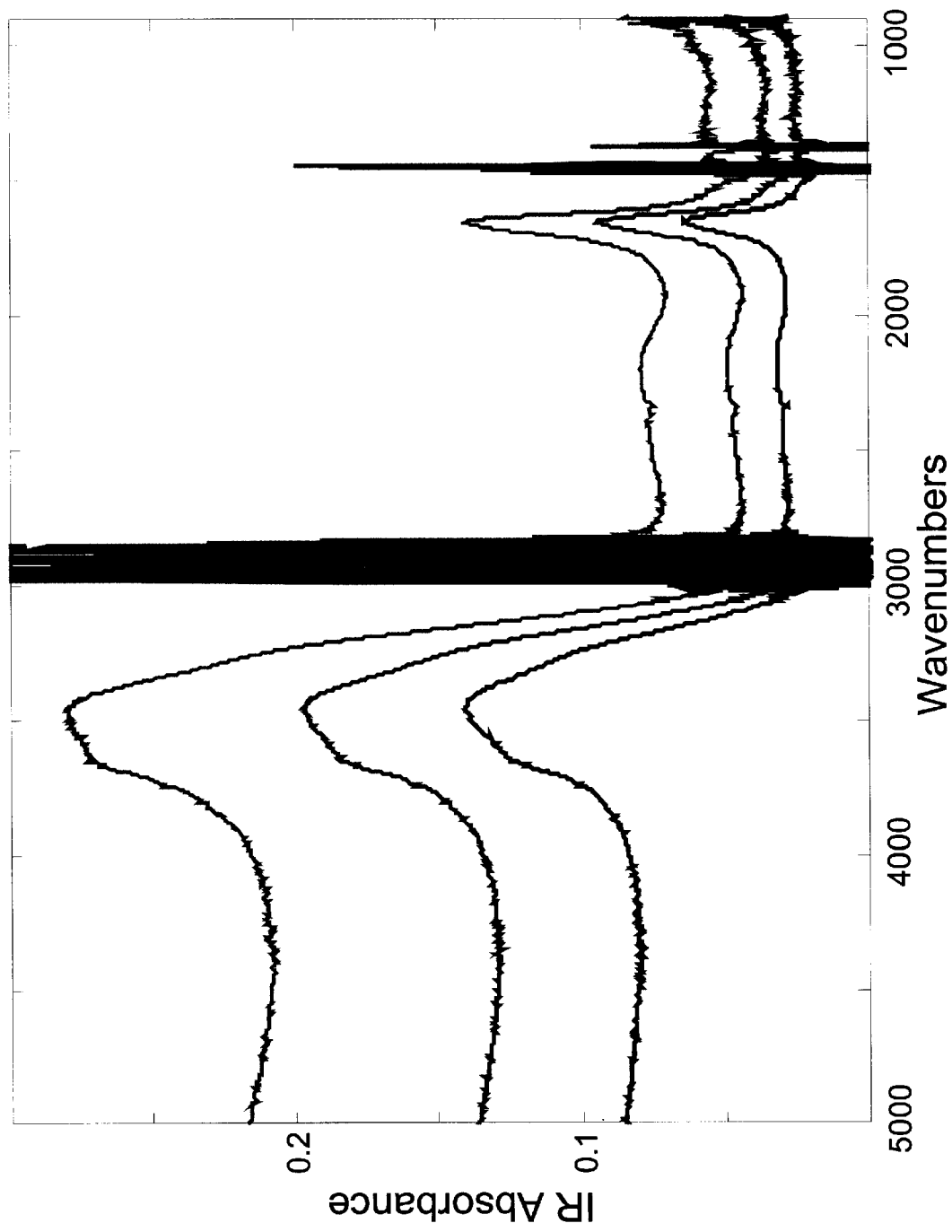
FIG. 6 shows difference spectra generated by subtracting the spectrum of Heidrun crude from spectra of the crude treaded with 1, 2 and 4% water.

Since the shape of the water absorptions is dependent on both the water level and the crude type, several example spectra are required to generate the water corrections. Water is added to selected reference crudes at levels ranging form 0.1 to 4% by volume. The samples are shaken, and allowed to settle. Spectra of the crude including any dispersed water are collected, as is a spectrum of the starting crude. FIG. 5 shows spectra (from bottom to top) of Heidrun crude, and the crude that was treated with 1, 2 and 4% water. Difference spectra are generated by subtracting the spectra of the starting crude from the spectra of the wet crudes so as to cancel features due to the organic crude components. Example difference spectra for the wet Heidrun crude samples are shown in FIG. 6. Similar difference spectra are generated for several different crudes. In this example, Al Rayyan, Fife, Heidrun, Hout, Odudu and Stag crudes were used to generate water difference spectra. These difference spectra become the columns of a matrix $X_c$. The matrix $X_c$ is first orthogonalized relative to the polynomials.

$$X'_w = X_w - U_p(U_p^{\,t}*X_w) \qquad [1]$$

The superscript t indicates matrix transpose. A singular value decomposition of the resultant matrix, $X'_w$, is then performed.

$$X_w' = U_w \Sigma_w V_w^{\,t} \qquad [2]$$

Figure 7:
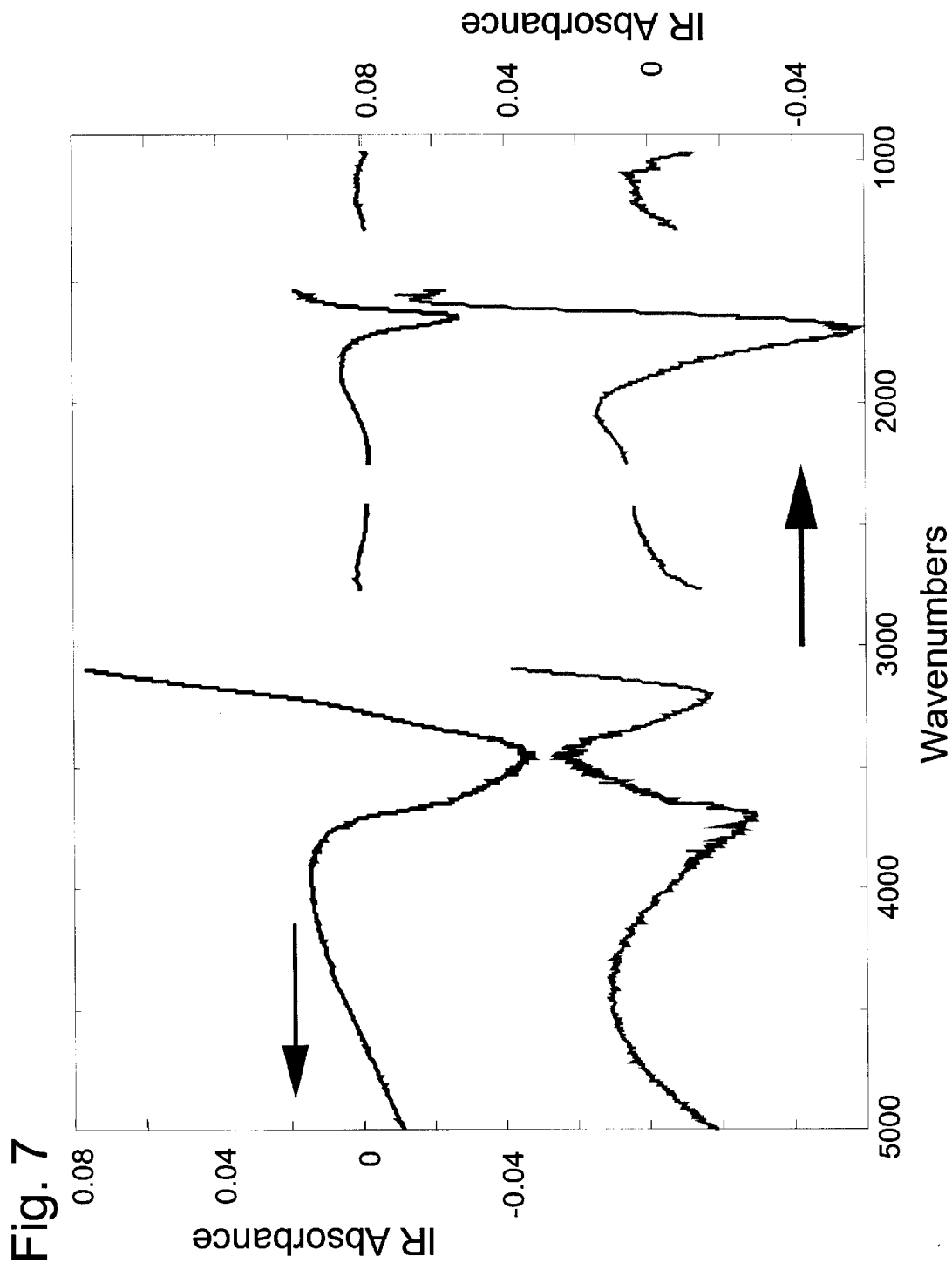
FIG. 7 shows the two correction vectors generated from the water difference spectra of FIG. 6.

The initial column vectors from the loadings matrix, $U_{w2}$ are used as correction vectors. For the case of water in crudes, the first two vectors are typically retained as corrections. These vectors are shown graphically in FIG. 7. The correction vectors are combined with the polynomials to form the corrections matrix, $U_C$.

$$U_c = [U_p, U_w] \qquad [3]$$

Figure 8:
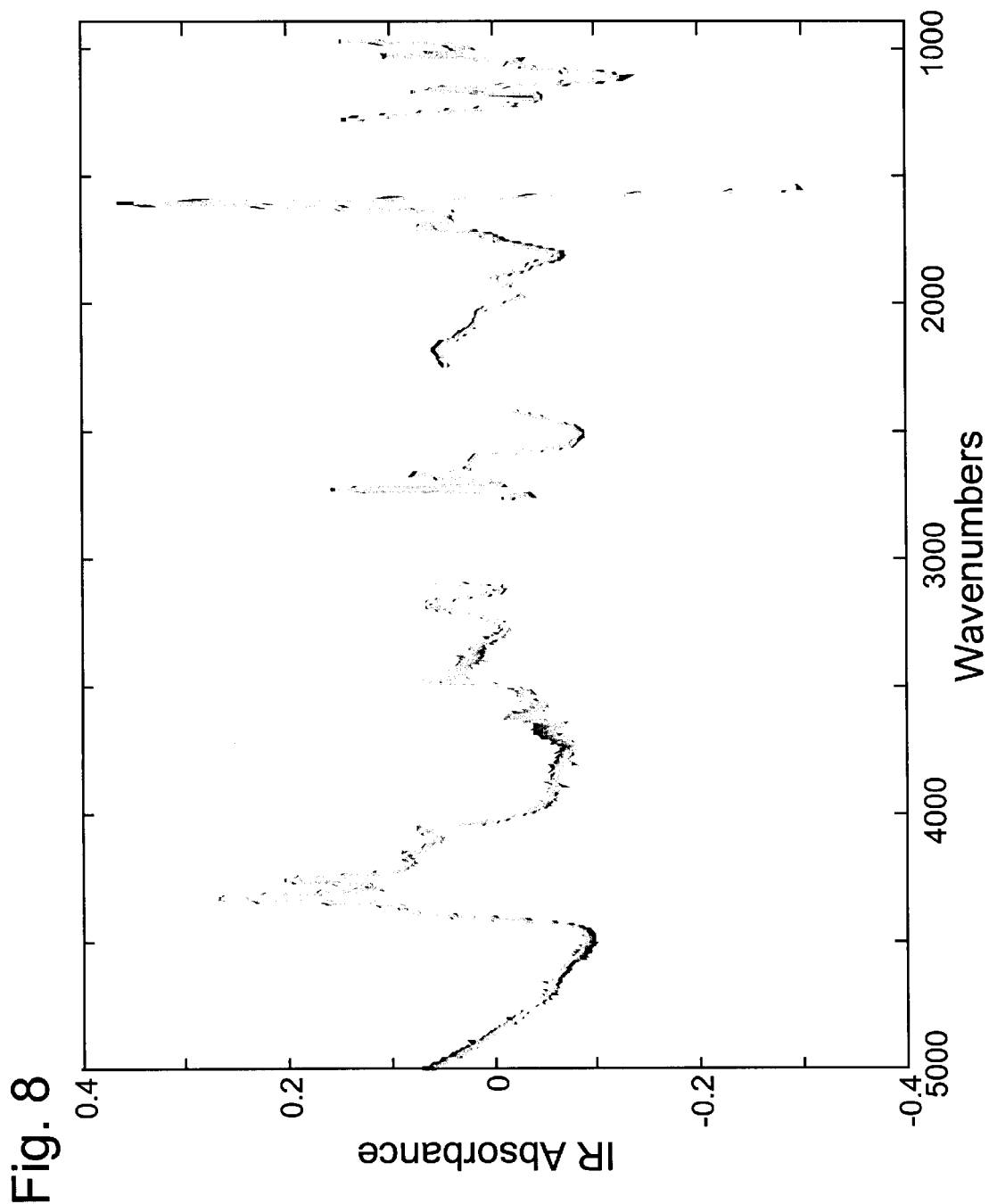
FIG. 8 shows the spectra of the 6 samples of Chocalho crude after orthogonalization to the polynomials and water correction vectors.

The column vectors of $U_C$ are orthonormal. When the spectra of the wet crudes (FIG. 4) are orthogonalized to the corrections (polynomials and dispersed water), the variations due to water and scattering are minimized (FIG. 8) such that the six spectra would yield essentially the same property predictions.

Other corrections may also be applied. For example, as discussed by Brown (U.S. Pat. No. 5,121,337), absorptions due to water vapor in the spectrometer light path can give rise to variations that affect the property predictions. Example spectra of water vapor can be collected, and used to generate a water vapor correction. The example spectra form the columns of a matrix $X_v$. This matrix is orthogonalized to all previously calculated corrections (e.g. polynomials and dispersed water).

$$X'_v = X_v - U_c(U_c^{\,t}*X_v) \qquad [4]$$

A singular value decompostion of the orthogonalized matrix is then calculated.

$$X'_v = U_v \Sigma_v V^t \qquad [5]$$

The initial columns of the loadings matrix, $U_v$, are then combined with the previously calculated corrections.

$$U_c = [U_c, U_v] \qquad [6]$$

For water vapor, typically only one loading vector will be retained. The column vectors of $U_c$ are orthonormal.

For different applications, different spectrometer types or different spectral ranges, the types of corrections that might be employed may be different. The above discussion is illustrative of how the corrections can be calculated. While polynomial corrections are typically calculated first, the order for which other corrections are calculated is arbitrary. For instance, the water vapor correction could be calculated before the correction for dispersed water.

In the database development mode, reference materials are analyzed via the detailed analysis, spectra of these materials are collected, and inspections for these materials are obtained. For crude oils, the detailed analysis is a crude assay. The inspections can include but are not limited to API gravity or specific gravity and viscosity. The viscosities must all be measured at the same temperature, but any temperature in the typical range used for crude analysis can be used. If the present invention is used for on-line analysis of a flowing crude stream, it might be preferable to measure the viscosities at the same 65° C. used for the spectra measurements.

If the spectra of the reference materials are collected using more than one cell, the spectra are scaled to a common pathlength. The relative pathlength of each cell is estimated by comparing the absorbance for a pure material such as toluene. The average pathlength is calculated, and each spectrum is scaled by the ratio of the average pathlength divided by the pathlength for the cell used to collect the spectrum. A CPSA model (U.S. Pat No. 5,121,337) can be used to estimate the pathlength for each spectrum.

The scaled spectra of the reference materials make up a matrix X of dimension f by n where n is the number of spectra. X is orthogonalized to the defined corrections.

$$X' = X - U_c(U_c^{t*}X) \qquad [7]$$

The scaled, orthogonalized spectra of the reference materials, I. The results from the detailed analysis, D, can be stored in the same database, or alternatively in a separate database. Each reference material is given a unique identifier to allow the spectrum, inspections and detailed analyses for a specific material to be associated.

In the analysis mode, a spectrum, $x_u$, and inspection data, $i_u$, for an unknown material are obtained. The spectrum and inspection data are collected under the same conditions as was used in collecting the spectra and inspection data for the reference materials.

The spectrum is orthogonalized relative to the same corrections used for the spectra of the reference materials.

$$x'_u = x_u - U_c(U_c^{t*}x_u) \qquad [8]$$

If, in the analysis mode, only spectral data is to be used, the orthogonalized spectrum, $x'_u$ is analyzed relative to the database using a least squares algorithm.

$$\min((\hat{x}_u - x_u)^t(\hat{x}_u - x_u)) \text{ where } \hat{x}_u = Xc_u \qquad [9]$$

The spectrum of the unknown material is fit as a linear combination of the spectra of the reference materials. The column vector $c_u$ contains the coefficients of the linear combination.

Since blending relationships typically assume positive proportions, a nonnegative least squares algorithm is preferred.

$$\min((\hat{x}_u - x_u)^t(\hat{x}_u - x_u) \text{ subject to constraint that } c_u \geq 0 \qquad [10]$$

A suitable algorithm is described by C. L. Lawson and R. J. Hanson (*Solving Least Squares Problems*, SIAM, 1995). A preferred algorithm is described by R. Bro and S. De Jong (*Journal of Chemometrics*, Vol. 11, 393–401,1997).

The coefficients calculated in [10] are normalized such that they sum to 1.

$$s = \sum_{i=1}^n c_i, \quad c'_u = \frac{c_u}{s} \qquad [11]$$

The coefficients, $c'_u$, calculated in [11] represent volume fractions of the reference materials in a "virtual blend", that is a blend that only exists in theory, preferably on a computer. These volume fractions and reference material properties are then used to calculate properties of the "virtual blend" using known blending relationships. These calculated properties for the "virtual blend" are predictions of the properties of the unknown material.

In the analysis mode of the preferred embodiment of this invention, inspection data is included in the analysis of the unknown material. The inspection data is converted to a volumetrically blendable form, and weighted relative to the spectral data.

To be used in the nonnegative least squares fit, the inspection data must be converted to a volumetrically blendable form. A property is volumetrically blendable if the value for a mixture can be calculated as the sum of the products of the volumetric proportions of the components times the component properties. Many properties are not volumetrically blendable, but can be transformed into a volumetrically blendable form. F is a function that converts the inspection, I, into a volumetrically blendable form, $\Lambda$.

$$\Lambda = F(I) \qquad [12]$$

Specific gravity is an example of a property that is volumetrically blendable. API Gravity is converted to specific gravity before use. Viscosity is first converted to a Viscosity Blending Number using a relationship of the form $$VBN = a + b \log(\log(v + c)) \qquad [13]$$

The volumetric blending number of the mixture is calculated as the sum of the component volume fractions times the component VBNs, and the viscosity for the mixture is calculated by inverting [13].

C. T. Baird (*Guide to Petroleum Product Blending*, HPI Consultants, Inc., 1989) describes Maxwell and Refutas blending indices that both have this form. For the purpose of this invention, the parameter a is set to 0 and the parameter b is set to 1. The parameter c is typically fixed at a value in the range from 0.6 to 0.8. If viscosities are assumed to blend on a weight basis, the VBN calculated from [13] would be multiplied by the specific gravity of the material to obtain a volumetrically blendable number. The method used to obtain volumetrically blendable numbers would typically be chosen to match that used by the program that manipulates the data from the detailed analysis.

The volumetrically blendable inspection data must be weighted relative to the spectral data for two reasons. First, there are typically many more spectral points than inspection results. Without weighting, the inspection results would contribute minimally to the sum of squares and thus minimally affect the calculated blend. Second, for some types of inspection measurements, the magnitude of the measurement error for the inspection data is level dependent. The weighting compensates for this variation.

In the preferred embodiment of this invention, the weighting for the inspections is calculated in the following manner:

The average variance for the corrected spectra in the database is calculated, $$\vec{V} = \frac{1}{n}\sum_{i=1}^n (x'_i)^t(x'_i) \qquad [14]$$

A nominal correlation coefficient for the least squares fit is selected, $R^2_{nom}$. A value in the range of 0.9992 to 0.9995 is typically used. This represents the fraction of the spectral variance that is expected to be fit in the least squares procedure. The per point accounted for variance is estimated as $$\varepsilon = R_{nom}^2 \frac{\overline{v}}{n} \quad [15]$$

If $i_u$ is the inspection data for the unknown, and the inspection is volumetrically blendable, the reproducibility of the inspection data at level $i_u$, $R(i_u)$ is determined using published reproducibility relationships. If the inspection data is not volumetrically blendable, then it is converted to a volumetrically blendable form, $\lambda_u = F(i_u)$, and the reproducibility is estimated in a volumetrically blendable form as $$R(\lambda_u) = F\left(i_u + \frac{R(i_u)}{2}\right) - F\left(i_u - \frac{R(i_u)}{2}\right) \quad [16]$$

The weighting for the inspection data is calculated as $$w = \frac{\alpha R}{2.77\varepsilon} \quad [17]$$

where R is $R(i_u)$ if the inspection data is volumetrically blendable, or $R(\lambda_u)$ if the inspection data is not volumetrically blendable. $\alpha$ is an adjustable parameter, which can be different for different inspection properties. A method of determining an appropriate value for $\alpha$ is discussed below.

The spectral data is augmented with the weighted, volumetrically blendable inspection data, and a least squares analysis is used to calculate a linear combination of the reference materials that provides the best fit to the combination.

$$\min\left(\left(\begin{bmatrix} \hat{x}_u \\ w\hat{\lambda}_u \end{bmatrix} - \begin{bmatrix} x_u \\ w\lambda_u \end{bmatrix}\right)^t \left(\begin{bmatrix} \hat{x}_u \\ w\hat{\lambda}_u \end{bmatrix} - \begin{bmatrix} x_u \\ w\lambda_u \end{bmatrix}\right)\right) \text{ where } \hat{x}_u = \quad [18]$$

$$Xc_u \text{ and } \hat{\lambda}_u = \Lambda c_u$$

The least squares fit is preferably calculated using a Nonnegative Least Squares algorithm as discussed above.

The linear combination calculated in [18] represents an initial estimate of the "virtual blend". The coefficients calculated in [18] are normalized using [11]. If the sum of the coefficients is sufficiently close to 1, then the results of [18] are taken as final. For FT-MIR spectra of crude oils, the summation value, s, must be between 0.9999 and 1.0001 for the coefficients of [18] to be taken as final. If the sum of the coefficients is not sufficiently close to 1, the spectral data in [18] is scaled by I/s and the minimization is repeated.

$$\min\left(\left(\begin{bmatrix} \hat{x}_u/s \\ w\hat{\lambda}_u \end{bmatrix} - \begin{bmatrix} x_u/s \\ w\lambda_u \end{bmatrix}\right)^t \left(\begin{bmatrix} \hat{x}_u/s \\ w\hat{\lambda}_u \end{bmatrix} - \begin{bmatrix} x_u/s \\ w\lambda_u \end{bmatrix}\right)\right) \text{ where } \hat{x}_u = \quad [19]$$

$$Xc_u \text{ and } \hat{\lambda}_u = \Lambda c_u$$

The coefficients calculated in [19] are normalized using [11]. This sequence is repeated (iterated) until the sum of the coefficients is sufficiently close to 1 or the maximum number of iterations is exceeded.

$\hat{X}_u$ is the calculated spectrum for the "virtual blend" which is the least squares estimate of the spectrum of the unknown. A goodness of fit estimate is given by $$R^2 = 1 - \frac{(\hat{x}_u - x_u)^t(\hat{x}_u - x_u)/(f - c - 1)}{(x_u - \overline{x}_u)^t(x_u - \overline{x}_u)/(f - 1)} \quad [20]$$

where c is the number of nonzero coefficients, and $\overline{x}_u$ is the average value of the spectral data for the unknown. Typically, the accuracy of property predictions will vary inversely with $R^2$. Depending on the accuracy requirements of the application, a minimum acceptable $R^2$ value, $R_{nom}^2$, is established. During analysis, if the calculated $R^2$ value exceeds $R_{nom}^2$, it is expected that the accuracy of the property predictions will be adequate. If the calculate $R^2$ for the unknown is less than $R_{nom}^2$, the predictions may be less accurate. For FT-MIR analysis of crude oils, depending on the exact frequency ranges used, $R_{nom}^2$ values of 0.9992 to 0.9995 are typically employed.

$\hat{\lambda}_u$ are the calculated volumetrically blendable inspections for the "virtual blend" which are the least squares estimates of the volumetrically blendable inspections for the unknown. The estimates for the inspections are obtained by applying the inverse relationship to [12], $$\hat{i}_u = F^{-1}(\hat{\lambda}_u) \quad [21]$$

One method for obtaining a suitable value for the parameter $\alpha$ in [17] is as follows. Initial values for a are selected for each inspection. A reference material in the database is removed and treated as an unknown. The spectrum and inspection data for this reference material are analyzed relative to the remaining reference materials using the procedure described above (equations [12] to [20]). The value of $\alpha$ is adjusted such that, for the spectra that are fit to the desired $R^2$, $$\sum \frac{2.77^2(\hat{i}_u - i_u)^t(\hat{i}_u - i_u)}{R(i_u)^2} \approx 1 \quad [22]$$

For FT-MIR analysis of crude oils, the summation is conducted over inspections corresponding to spectra that were fit to $R_{nom}^2$ or better. This value of $\alpha$ provides that the error distribution for the predicted inspection has the same standard deviation as the reference method reproducibility. A higher value of $\alpha$ can be used to provide a prediction with a smaller standard deviation if the quality of the inspection data is better than reproducibility. A smaller value of a will result in a larger inspection property prediction error.

Fitting to Subsets of the Database

While unknowns can be analyzed relative to the entire database, it is sometimes useful to conduct the analysis relative to a subset of the database. The subset can be chosen based on prior knowledge as to the expected similarity of the unknown to members of the subset. For example, a new sample of a particular grade of crude oil might be analyzed relative to a subset consisting of reference samples of the same grade for which assays had been conducted so as to determine whether the properties of the current cargo is consistent with those of previous cargoes. Similarly, a crude oil obtained from a certain point of origin can be analyzed using a subset consisting of known crudes from the same geographic region.

Prediction of Qualities Using Blending Rules

Prediction of qualities is done using the "virtual blend" composition calculated using the methodology described above and known blending relationships. The predictions may be done using software designed to calculate qualities for real blends of materials. Software capable of doing these "blend" calculations is commercially available from Haverly Systems Inc., HPI Consultants Inc., and Aspentech Inc. Many oil companies have similar "in-house" systems. Examples of methodologies that can employed for the "blend" to calculations are described below.

For volumetrically blendable properties, the predicted quality, ^, is calculated as the weighted sum of the qualities of the reference materials.

$$\hat{q} = q'c_u = \sum_{i=1}^{c} q_i c_i \qquad [23]$$

where q is a column vector containing the qualities for the reference materials, and $q_i$ is the quality for the $i^{th}$ reference material. Volumetrically blendable qualities include, but are not limited to:

volume % yield specific gravity saturates or aromatics measured by FIA (ASTM D1319)

elemental data expressed as pounds per barrel refractive index

Many properties are blendable on a weight (gravimetric) basis. For properties that are blendable on a weight basis, the volumetric coefficients calculated from the least squares fit are multiplied by the specific gravities of the corresponding reference materials. The predicted quality, q̂, is calculated as follows:

$$\hat{q} = \frac{q^t P c_u}{\rho_u} = \frac{\sum_{i=1}^{c} q_i \rho_i c_i}{\sum_{i=1}^{c} \rho_i c_i} \qquad [24]$$

P is a diagonal matrix containing the specific gravities of the reference materials, $\rho_i$. $\hat{\rho}_u$ is the predicted specific gravity for the unknown being analyzed. Weight blendable properties include but are not limited to:

API Gravity

Weight % yield

Elemental data expressed as weight percent or PPM on a weight basis

Neutralization number

Compositional data derived from GC or HPLC analysis

Some properties cannot be blended directly on either a volume or weight basis. C. T. Baird (*Guide to Petroleum Product Blending*, HPI Consultants, Inc., 1989) describes methods that are used to blend various nonlinear properties, and how such methods are developed. In most instances, these methods involve applying a mathematical function to calculate a blending number or blending index, volumetrically or gravimetrically blending these numbers/indices, and then calculating the quality for the blend using the inverse of the mathematical function. The Refutas blending indices mentioned above are one example of blending nonlinear properties. Cold flow properties such as pour point, cloud point and freeze point are typically calculated using a blending index approach, as are such properties as flash point.

Distributed qualities, i.e. quality values as a function of distillation temperature, are calculated as follows. The distillation yield curves (volume % and weight %) and the quality data collected for distillate cuts are fit to smooth curves, typically using spline fits. Yield and quality values are calculated at ~5° C. intervals based on the smooth curve fits. The volumetric, gravimetric or nonlinear blending methods are applied to the data at each temperature interval to produce an estimate for the distributed qualities.

EXAMPLES

In the following examples, X consists of the FT-MIR spectra of 297 crude oils collected at 65° C. using cells with $CaF_2$ windows and a nominal 0.2 mm pathlength. X covers the regions from 4685.2 to 3586.0 $cm^{-1}$, 2608.3 to 2524.4 $cm^{-1}$, 2238.9 to 1537.0 $cm^{-1}$ and 1341.2 to 1045.2 $cm^{-1}$. The regions around 3000 $cm^{-1}$ and between 1537.0 and 1341.2 $cm^{-1}$ are excluded to avoid absorbances that exceed the linear response range of the instrument. The region around 2400 $cm^{-1}$ is excluded to avoid interferences due to atmospheric carbon dioxide. At this pathlength, the region above 4685.2 $cm^{311}$ does not contain sufficiently strong absorbances to be useful in the analysis. The $CaF_2$ windows block transmission at frequencies below about 1045.2 $cm^{-1}$.

Baseline polynomials, $U_p$, were generated as shown in FIG. 2. Constant, linear, quadratic, cubic and quartic terms are used in the 4685.2 to 3586.0 $cm^{-1}$ region. Separate constant, linear, quadratic and cubic terms are generated to span the region between 2608.3 and 1537.0 $cm^{-1}$. Constant, linear, quadratic and cubic terms are used in the region from 1341.2 to 1045.2 $cm^{-1}$.

Two types of corrections were employed. A correction for water in the crude samples was generated as discussed herein above. 28 difference spectra were used and two correction terms were retained. A correction for water vapor in the instrument light path was also generated as discussed herein above. 60 example spectra of water vapor were used, and one correction term was generated. The crude spectra in X are orthogonalized to the polynomials and corrections as discussed herein above to produce the corrected spectra, X'.

A cross validation approach was used to evaluate the predictive capabilities of this method. One of the 297 corrected crude spectra is removed from X' and treated as an unknown. If inspections are used, the corresponding inspection data is removed from I. The spectrum or spectrum and inspections are analyzed as described herein above to calculate a "virtual blend" based on the remaining crudes. The calculated blend compositions are then used to estimate crude qualities using known blending relationships. The process is repeated 297 times, leaving each crude out as an unknown once. Since the spectra of the crudes with the more extreme compositions cannot be fit adequately when they are left out of the database, the evaluation of the method was made using only those crudes that were adequately fit, i.e. crudes for which $R^2$ from equation [18] is greater than or equal to 0.9992.

To demonstrate the effect of including inspection data in the fit, three sets of data are presented. Set 1 is for fits done using only the IR data. Set 2 is for fits that include API Gravity with a weighting coefficient, α (equation [15]) of 30.1578. Set 3 is for fits that include API Gravity with a weighting coefficient, α, of 30.7496 and viscosity at 40° C. with a weighting coefficient of 87.1783.

Figure 9:
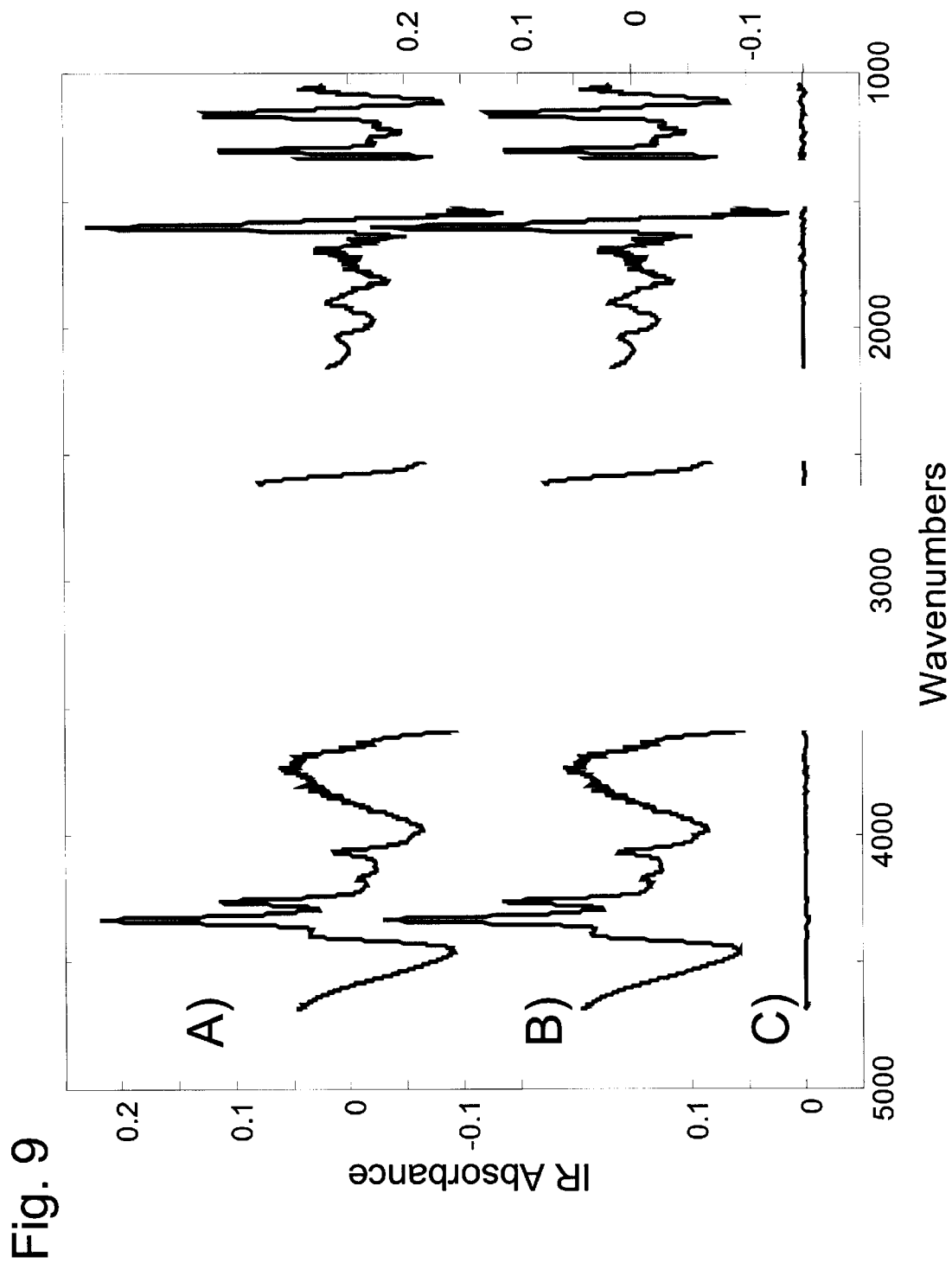
FIG. 9 a) shows the spectrum of a Kuwait crude sample assayed in 1999, b) shows the fit to that spectrum and c) shows the difference between the spectrum and the fit.

FIG. 9a shows the spectrum of a sample of Kuwait crude obtained in 1999. The spectrum has been orthogonalized to the polynomial and correction terms. Table 2 shows the "Virtual Blends" that are calculated based on fits of this spectra to 295 crude spectra in the database, excluding a newer Kuwait '00 sample.

TABLE 2

Analysis of Kuwait '99 Crude Sample

| Reference Crude | Assay Year | Nearness Index | Set 1 IR Only Entire Library | Set 2 IR & API Entire Library | Set 3 IR, API & Visc Entire Library | Set 4 IR, API & Visc Middle East Crudes |
|---|---|---|---|---|---|---|
| AL SHAHEEN | 00 | 12 | 0.56 | | 0.23 | |
| ARAB LIGHT | 97 | 4 | 9.95 | 11.07 | 6.44 | |
| ARAB MEDIUM | 97 | 3 | 25.88 | 22.97 | 17.46 | 19.27 |
| ARAB EXTRA LIGHT | 96 | 24 | 2.30 | 2.00 | 1.90 | 2.95 |
| BASRAH | 99 | 5 | 22.82 | 23.48 | 25.48 | 29.30 |
| BUFFALO | 99 | 220 | 0.63 | 1.76 | | |
| EZZAOUIA | 00 | 150 | | 0.78 | 0.92 | |
| KHAFJI | 99 | 9 | 1.46 | 3.19 | 10.28 | 9.67 |
| KIRKUK | 97 | 22 | 10.48 | 12.29 | 13.68 | 15.07 |
| LALANG | 00 | 202 | 0.58 | | | |
| MURBAN | 97 | 51 | | | 0.68 | |
| PALANCA | 97 | 61 | | 0.16 | | |
| RATAWI | 98 | 29 | 13.94 | 14.13 | 14.98 | 22.44 |
| SYRIAN LIGHT | 99 | 42 | 2.45 | | 0.69 | 1.30 |
| TANTAWAN | 97 | 240 | | 0.02 | | |
| TIERRA DEL FUEGO | 99 | 182 | 1.51 | | | |
| WYTCH FARM | 98 | 111 | 0.51 | 0.63 | 2.37 | |
| XAN | 00 | 148 | 6.46 | 6.07 | 4.90 | |
| XIKOMBA | 99 | 95 | 0.48 | 1.45 | | |
| Fit R-squared | | | 0.9999 | 0.9999 | 0.9999 | 0.9999 |
| API (Predicted - Actual) | | | | −0.1 | −0.3 | −0.3 |
| Visc40 C (Predicted - Actual) | | | | | −0.11 | −0.12 |

FIG. 9b shows the least squares fit which is generated as the weighted sum of the spectra for the crudes listed in Table 2 under Set 3. FIG. 9c shows the difference between the spectrum of the crude and the fit. The $R^2$ for the fit is greater than 0.9999.

The 295 crudes used in the fit include a sample of Kuwait crude obtained in 1998. This example demonstrates how this invention can be used to track changes in crude quality with time. If the crude were unchanged, the coefficient associated with the Kuwait '98 crude would be expected to exceed 90%. In fact, the Kuwait '98 spectrum is not included in the fit, indicating that a significant change in crude quality has occurred. This is confirmed by the change in he API Gravity of the crude from 29.8° to 30.9°. This invention predicts an API Gravity in the range of 30.6°–30.8° depending on whether inspection data is included. 30.6°–30.8° agrees with the measured value of 30.9° to within the reproducibility of the API Gravity test method.

Table 3 shows the predicted whole crude properties, and Tables 4 and 5 shows predicted properties for representative distillate cuts.

TABLE 3

Whole Crude Quality Predictions for Kuwait '99 Crude

| Assay Year | 1998 | 1999 | Set 1 IR Only Entire Library | Set 2 IR & API Entire Library | Set 3 IR, API & Visc Entire Library | Set 4 IR, API & Visc Middle East Crudes |
|---|---|---|---|---|---|---|
| WHOLE CRUDE PROPERTIES | | | | | | |
| API Gravity | 29.8 | 30.9 | 30.6 | 30.8 | 30.6 | 30.6 |
| Specific Gravity | 0.8773 | 0.8713 | 0.8727 | 0.8721 | 0.8729 | 0.8729 |
| Conradson Carbon (wt %) | 6.7 | 5.9 | 6.5 | 6.5 | 6.6 | 6.5 |
| Nitrogen (wt %) | 0.15 | 0.09 | 0.14 | 0.14 | 0.13 | 0.14 |
| Sulfur (wt %) | 2.77 | 2.50 | 2.68 | 2.68 | 2.69 | 2.71 |
| Viscosity at 40 C cst | 11.97 | 10.68 | 10.09 | 9.90 | 10.57 | 10.56 |
| Viscosity at 50 C cst | 9.21 | 8.27 | 7.85 | 7.69 | 8.19 | 8.17 |
| Viscosity at 60 C cst | 7.30 | 6.58 | 6.29 | 6.15 | 6.53 | 6.51 |
| Neutralization Number | 0.2 | 0.2 | 0.1 | 0.1 | 0.1 | 0.1 |
| Nickel (ppm) | 11 | 9 | 13 | 13 | 13 | 13 |
| Vanadium (ppm) | 36 | 31 | 48 | 47 | 46 | 37 |

TABLE 4

Quality Predictions for Kuwait '99 Crude Light Distillate Cuts

| Assay Year | 1998 | 1999 | Set 1 IR Only Entire Library | Set 2 IR & API Entire Library | Set 3 IR, API & Visc Entire Library | Set 4 IR, API & Visc Middle East Crudes |
|---|---|---|---|---|---|---|
| Light Virgin Naphtha (−200 to 160 F) | | | | | | |
| Volume Yield | 7.0 | 8.6 | 7.4 | 7.5 | 7.6 | 7.6 |
| Benzene (vol %) | 0.28 | 0.24 | 0.17 | 0.15 | 0.17 | 0.15 |
| C5 Isoparaffins (vol %) | 12.88 | 13.36 | 14.71 | 14.65 | 14.74 | 14.82 |
| C6 Isoparaffins (vol %) | 20.88 | 18.38 | 19.95 | 20.13 | 19.36 | 19.57 |
| C7 Isoparaffins (vol %) | 1.13 | 1.26 | 0.26 | 0.23 | 0.41 | 0.40 |
| C5 n-paraffins (vol %) | 21.84 | 20.58 | 21.96 | 21.87 | 21.58 | 21.63 |
| C6 n-paraffins (vol %) | 14.98 | 12.50 | 12.39 | 12.34 | 12.27 | 12.27 |
| Heavy Virgin Naphtha (160 to 360 F) | | | | | | |
| Volume Yield | 17.2 | 16.3 | 17.3 | 17.6 | 17.0 | 17.0 |
| Sulfur (wt %) | 0.04 | 0.02 | 0.07 | 0.07 | 0.07 | 0.07 |
| API Gravity | 58.4 | 59.0 | 58.8 | 59.0 | 58.8 | 58.8 |
| Benzene (vol %) | 0.28 | 0.27 | 0.30 | 0.28 | 0.28 | 0.25 |
| Naphthenes (vol %) | 23.13 | 23.06 | 23.49 | 23.17 | 23.20 | 23.21 |
| Aromatics (vol %) | 11.20 | 11.90 | 11.42 | 11.28 | 11.64 | 11.71 |
| n-Octanes (vol %) | 7.17 | 8.13 | 7.46 | 7.56 | 7.54 | 7.46 |
| Isooctanes (vol %) | 9.25 | 9.32 | 9.03 | 9.10 | 8.98 | 8.97 |
| C8 Cyclohexanes (vol %) | 2.05 | 2.36 | 2.22 | 2.24 | 2.21 | 2.19 |
| C8 Aromatics (vol %) | 4.23 | 4.84 | 4.09 | 4.07 | 4.26 | 4.29 |
| Kerosene (320 to 500 F) | | | | | | |
| Volume Yield | 16.8 | 15.8 | 17.0 | 17.1 | 16.8 | 16.9 |
| Sulfur (wt %) | 0.29 | 0.27 | 0.34 | 0.34 | 0.35 | 0.33 |
| API Gravity | 45.4 | 46.2 | 45.7 | 45.8 | 45.8 | 45.7 |
| Pour Point (deg F) | −57 | −48 | −55 | −55 | −55 | −55 |
| Cloud Point (deg F) | −47 | −42 | −45 | −45 | −45 | −45 |
| Freeze Point (deg F) | −42 | −38 | −39 | −39 | −39 | −40 |
| Cetane Index 1990 | 49 | 51 | 50 | 50 | 50 | 50 |
| Smoke Point | 24 | 24 | 24 | 24 | 24 | 24 |
| Jet (360 to 530 F) | | | | | | |
| Volume Yield | 15.6 | 14.9 | 16.1 | 16.1 | 15.8 | 15.9 |
| Sulfur (wt %) | 0.46 | 0.46 | 0.53 | 0.52 | 0.53 | 0.51 |
| API Gravity | 42.7 | 43.7 | 43.1 | 43.1 | 43.2 | 43.1 |
| Pour Point (deg F) | −40 | −32 | −39 | −39 | −39 | −39 |
| Cloud Point (deg F) | −31 | −27 | −30 | −30 | −29 | −30 |
| Freeze Point (deg F) | −26 | −24 | −24 | −24 | −24 | −25 |
| Cetane Index 1990 | 51 | 54 | 52 | 52 | 52 | 52 |
| Smoke Point | 22 | 23 | 23 | 23 | 22 | 22 |
| Aromatics (vol %) | 12.29 | 15.30 | 16.87 | 16.93 | 16.75 | 16.75 |
| Viscosity at 40 C cst | 1.66 | 1.68 | 1.70 | 1.70 | 1.70 | 1.70 |
| Viscosity at 100 C cst | 0.81 | 0.82 | 0.82 | 0.82 | 0.82 | 0.82 |
| Viscosity Blending Number 100 C | 0.23 | 0.31 | 0.43 | 0.42 | 0.43 | 0.42 |

TABLE 5

Quality Predictions for Kuwait '99 Crude Heavy Distillate Cuts

| Assay Year | 1998 | 1999 | Set 1 IR Only Entire Library | Set 2 IR & API Entire Library | Set 3 IR, API & Visc Entire Library | Set 4 IR, API & Visc Middle East Crudes |
|---|---|---|---|---|---|---|
| Diesel (530 to 650 F) | | | | | | |
| Volume Yield | 10.1 | 10.4 | 11.0 | 10.9 | 10.9 | 10.9 |
| Sulfur (wt %) | 1.74 | 1.59 | 1.77 | 1.78 | 1.76 | 1.74 |
| Neutralization Number | 0.2 | 0.1 | 0.1 | 0.1 | 0.1 | 0.1 |
| API Gravity | 33.2 | 33.7 | 33.3 | 33.3 | 33.4 | 33.4 |
| Pour Point (deg F) | 21.1 | 24.2 | 22.2 | 22.2 | 22.2 | 21.9 |
| Cloud Point (deg F) | 28.0 | 28.3 | 29.0 | 28.9 | 29.0 | 28.7 |
| Cetane Index 1990 | 56.9 | 58.1 | 57.0 | 57.0 | 57.3 | 57.3 |
| Nitrogen (wt %) | 0.0066 | 0.0084 | 0.0082 | 0.0082 | 0.0082 | 0.0084 |
| Renactive Index (67 C) | 1.4541 | 1.4539 | 1.4561 | 1.4561 | 1.4556 | 1.4556 |
| Viscosity at 40 C cst | 4.70 | 4.55 | 4.65 | 4.64 | 4.66 | 4.67 |
| Viscosity at 100 C cst | 1.60 | 1.60 | 1.59 | 1.59 | 1.60 | 1.60 |
| Viscosity Blending Number 100 C | 9.04 | 9.06 | 9.00 | 8.97 | 9.01 | 9.01 |

TABLE 5-continued

Quality Predictions for Kuwait '99 Crude Heavy Distillate Cuts

| Assay Year | 1998 | 1999 | Set 1 IR Only Entire Library | Set 2 IR & API Entire Library | Set 3 IR, API & Visc Entire Library | Set 4 IR, API & Visc Middle East Crudes |
|---|---|---|---|---|---|---|
| Vacuum Gas Oil (650 to 1050 F) | | | | | | |
| Volume Yield | 29.2 | 29.7 | 29.0 | 28.7 | 29.0 | 29.0 |
| Sulfur (wt %) | 3.18 | 2.97 | 3.11 | 3.13 | 3.09 | 3.10 |
| Neutralization Number | 0.2 | 0.2 | 0.2 | 0.2 | 0.2 | 0.2 |
| API Gravity | 21.2 | 21.6 | 21.3 | 21.2 | 21.4 | 21.3 |
| Pour Point (deg F) | 96 | 88 | 92 | 92 | 93 | 92 |
| Nitrogen (wt %) | 0.086 | 0.090 | 0.085 | 0.085 | 0.084 | 0.086 |
| Basic Nitrogen (wt %) | 0.023 | 0.027 | 0.026 | 0.026 | 0.026 | 0.027 |
| Nickel (ppm) | 0.062 | 0.027 | 0.064 | 0.066 | 0.064 | 0.065 |
| Vanadium (ppm) | 0.221 | 0.024 | 0.189 | 0.190 | 0.171 | 0.150 |
| Refractive Index (67 C) | 1.4960 | 1.4970 | 1.4960 | 1.4960 | 1.4960 | 1.4960 |
| Analine Point (deg F) | 173.9 | 172.7 | 174.5 | 174 | 174.7 | 174.7 |
| Conradson Carbon (wt %) | 0.88 | 0.74 | 0.80 | 0.80 | 0.78 | 0.79 |
| Viscosity at 79.4 C cst | 13.53 | 13.43 | 13.11 | 13.13 | 13.12 | 13.08 |
| Viscosity at 100 C cst | 7.76 | 7.70 | 7.53 | 7.54 | 7.54 | 7.52 |
| Viscosity Blending Number 100 C | 22.08 | 22.04 | 21.90 | 21.91 | 21.91 | 21.89 |
| Saturates (wt %) | 44.2 | 44.1 | 44.1 | 43.7 | 44.1 | 44.0 |
| 1-Ring Aromatics (wt %) | 16.7 | 17.1 | 17.4 | 17.4 | 17.3 | 17.3 |
| 2-Ring Aromatics (wt %) | 20.2 | 17.4 | 18.7 | 18.8 | 18.7 | 18.7 |
| 3-Ring Aromatics (wt %) | 9.0 | 9.3 | 9.0 | 9.1 | 9.1 | 9.1 |
| 4-Ring Aromatics (wt %) | 6.0 | 7.1 | 6.6 | 6.6 | 6.6 | 6.6 |
| Polars (wt %) | 3.9 | 5.0 | 4.3 | 4.3 | 4.3 | 4.3 |
| 1-Ring Aromatic Cores (wt %) | 2.6 | 2.8 | 2.6 | 2.6 | 2.6 | 2.6 |
| 2-Ring Aromatic Cores (wt %) | 5.8 | 5.3 | 5.6 | 5.7 | 5.6 | 5.6 |
| 3-Ring Aromatic Cores (wt %) | 4.8 | 4.7 | 5.0 | 5.0 | 5.0 | 5.0 |
| 4-Ring Aromatic Cores (wt %) | 3.1 | 4.1 | 3.5 | 3.5 | 3.5 | 3.5 |
| Polar Cores (wt %) | 2.3 | 1.8 | 2.0 | 2.0 | 2.0 | 1.9 |
| Vacuum Resid (1050 F+) | | | | | | |
| Volume Yield | 20.9 | 20.1 | 19.3 | 19.2 | 19.6 | 19.6 |
| Sulfur (wt %) | 5.6 | 5.4 | 5.8 | 5.8 | 5.8 | 5.6 |
| Neutralization Number | 0.3 | 0.3 | 0.2 | 0.2 | 0.2 | 0.2 |
| API Gravity | 3.8 | 2.8 | 3.1 | 3.1 | 3.0 | 3.2 |
| Pour Point (deg F) | 155.2 | 172.5 | 156.5 | 157.2 | 160.0 | 160.1 |
| Nitrogen (wt %) | 0.5 | 0.3 | 0.5 | 0.5 | 0.4 | 0.4 |
| Refractive Index (67 C) | 1.5 | 1.5 | 1.5 | 1.5 | 1.5 | 1.5 |
| Analine Point (deg F) | 181.6 | 178.6 | 180.1 | 179.9 | 180.6 | 181.2 |
| Mean Average Boiling Point (deg F) | 1265.0 | 1257.0 | 1262.0 | 1262.0 | 1263.0 | 1262.0 |
| Conradson Carbon (wt %) | 25.6 | 23.4 | 26.9 | 27.0 | 26.8 | 26.3 |
| Viscosity at 79.4 C cst | 69070 | 67170 | 10760 | 11140 | 11710 | 10130 |
| Viscosity at 100 C cst | 9663 | 9449 | 13720 | 14150 | 14930 | 13280 |
| Viscosity Blending Number 100 C | 43.2 | 43.2 | 43.7 | 43.8 | 43.9 | 43.7 |
| Viscosity at 135 C cst | 852 | 839 | 1084 | 1112 | 1173 | 1080 |

Note that the quality predictions for the distillate cuts are being made from measurements of the whole crude sample. In most instances, the predicted qualities agree with those measured to within the reproducibility of the reference measurement. For this example, the predictions do not vary significantly between the fit based solely on the IR spectra (Set 1) and the fits which included inspection data (Sets 2–4).

The Kuwait '99 example demonstrates a significant difference between the methodology of the current invention and that described by B. Descales, D. Lambert, J. LLinas, A. Martens, S. Osta, M. Sanchez and S. Bages (U.S. Pat. No. 6,070,128 May 30, 2000). Euclidean distances between the 295 corrected reference spectra and the corrected spectrum of the Kuwait '99 sample were calculated, and the reference samples were ranked in terms of increasing distance. The results are shown in the column labeled Nearness Index in Table 3. The method of Descales, et al. utilizes on those references that are closest to the unknown. With the method of this invention, the reference crude with the smallest Euclidean distance, a Basrah crude assayed in 2000, was not included in the fit, and references that are 22nd and 29th closest make significant contributions to the fit.

The right most column in Tables 2–5 show data for a case where the references used in the fit are restricted to a subset which originate in the Middle East. Note that the property predictions obtained using the subset are almost indistinguishable from those obtained using the full library. The ability to fit the crude data using a subset can be employed to infer additional information about the unknown.

The use of fits to subsets to infer information is further illustrated by the following example. In this case, data for a Syrian Light crude sample assayed in 2000 is fit to only one reference, data for a Syrian Light crude sample assayed in 1999. The results of the fits are shown in Table 6.

TABLE 6

Analysis of Syrian Light '00 Sample

| Reference Crude | Assay Year | Set 1 IR Only Entire Library | Set 2 IR & API Entire Library | Set 3 IR, API & Visc Entire Library |
|---|---|---|---|---|
| SYRIAN LIGHT | 99 | 100.00 | 100.00 | 100.00 |
| Fit R-squared | | 0.9997 | 0.9997 | 0.9997 |
| API (Predicted - Actual) | | | 0.1 | 0.1 |
| Visc40 C (Predicted - Actual) | | | | 0.09 |

Figure 10:
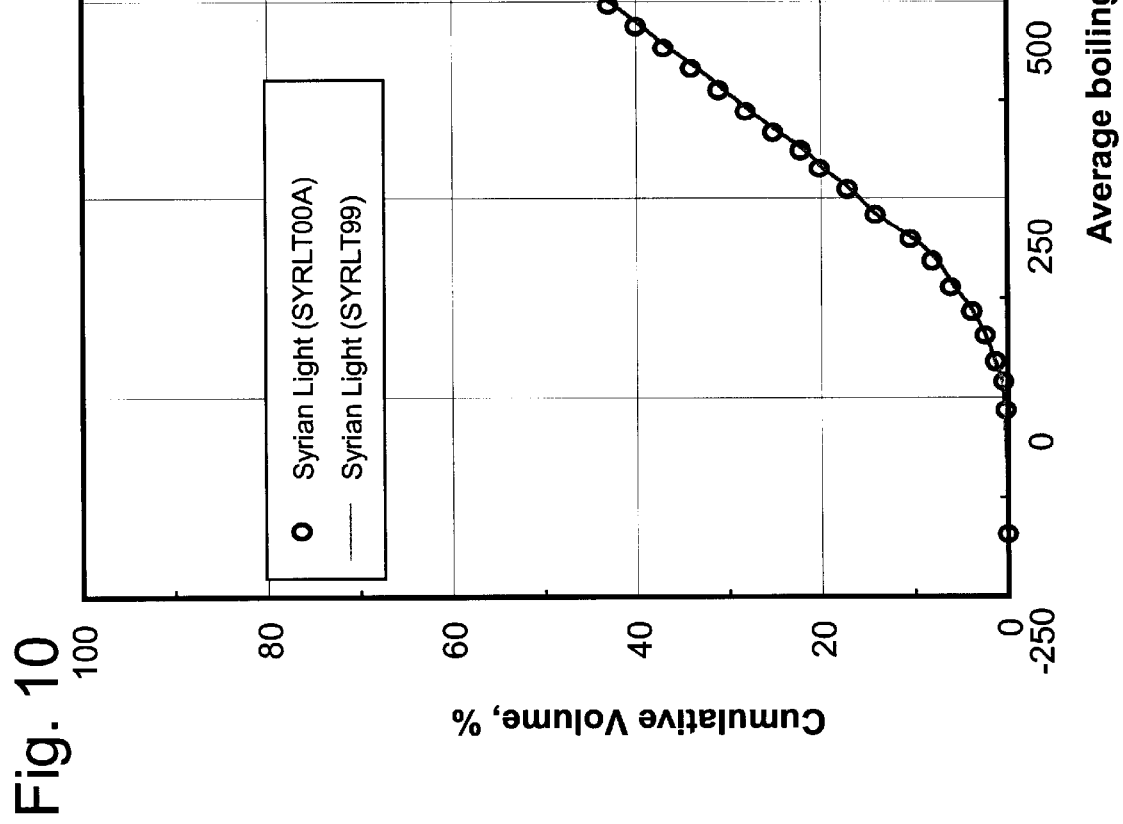
FIG. 10 shows yield curves for two Syrian Light crude samples demonstrating their similarity.

The data for the '00 sample can be fit with an $R^2$ of 0.9997. If inspection data is included, it is also fit to better than the precision of the reference measurement. The fact that the data for the '00 sample can be adequately fit with data from only the '99 sample can be used to infer that minimal change in crude quality has occurred. This inference is shown to be correct by the whole crude data in Table 7, and by the cumulative volume yield data shown in FIG. 10.

TABLE 7

Whole Crude Data for Syrian Light

| Assay Year | '99 | '00 |
|---|---|---|
| Property | | |
| API Gravity | 36.1 | 36 |
| Pour Point | 35 | 25 |
| Viscosity 40 C | 5.29 | 5.19 |
| Viscosity 50 C | 4.23 | 4.24 |
| Conradson Carbon | 2.28 | 2.63 |
| Sulfur wt % | 0.71 | 0.75 |
| Neutralization Number | 0.05 | 0.07 |
| Nickel (ppm) | 6.2 | 7.7 |
| Vanadium (ppm) | 7.4 | 8.7 |

Table 8 shows the "Virtual Blends" that are calculated based on fits of a spectrum of a Suez Mix crude sample obtained in 1998.

TABLE 8

Analysis of Suez Mix Crude

| Crude | Assay Year | Country of Origin | Set 1 IR Only | Set 2 IR & API | Set 3 IR, API & Visc |
|---|---|---|---|---|---|
| ASHTART | 00 | TUNISIA | 2.3 | 2.1 | 3.4 |
| ARAB SUPER LIGHT | 00 | S. ARABIA | | | 0.4 |
| BELAYIM | 97 | EGYPT | 43.0 | 42.9 | 45.3 |
| CABINDA | 97 | ANGOLA | 2.5 | 2.4 | 2.4 |
| DIDON | 98 | TUNISIA | 8.1 | 6.9 | 6.8 |
| DUBAI | 96 | DUBAI | 1.1 | | |
| SUEZ MIX | 95 | EGYPT | 13.1 | 14.8 | 11.0 |
| HOUT | 96 | NEUTZONE | 10.1 | 8.4 | 7.4 |
| IMA | 99 | NIGERIA | 2.0 | 1.9 | 1.9 |
| KLAME | 98 | ANGOLA | 10.2 | 10.5 | 10.1 |
| KIRKUK | 97 | IRAQ | 4.2 | 3.9 | 3.1 |
| MARIB LIGHT | 99 | N. YEMEN | 0.1 | 0.7 | 0.9 |
| MOUDI | 99 | CAMEROON | 2.0 | 1.9 | 2.2 |
| UPPER ZAKUM | 98 | ABUDHABI | 1.2 | 3.5 | 5.4 |
| Fit R-squared | | | 0.9999 | 0.9999 | 0.9999 |
| API (Predicted - Actual) | | | | −0.1 | −0.1 |
| Visc40 C (Predicted - Actual) | | | | | 0.02 |

The data for this crude was fit to reference data for 107 crudes from Africa and the Middle East. All 3 fits had $R^2$ values greater than 0.9999. This example demonstrates how this invention could be used to analyze a crude mix. Note that, even though a previous 1995 Suez Mix sample is represented in the database, it is not sufficiently similar to the current sample to contribute significantly to the fits. The predicted whole crude qualities and distributed qualities are shown in Tables 9–11.

TABLE 9

Whole Crude Quality Predictions for Suez Mix '98 Crude

| Assay Year | 98 | Set 1 IR Only | Set 2 IR & API | Set 3 IR, API & Visc |
|---|---|---|---|---|
| WHOLE CRUDE PROPERTIES | | | | |
| API Gravity | 30.6 | 30.4 | 30.5 | 30.5 |
| Specific Gravity | 0.8729 | 0.8740 | 0.8737 | 0.8734 |
| Conradson Carbon (wt %) | 5.8 | 5.8 | 5.8 | 5.8 |
| Sulfur (wt %) | 1.70 | 1.65 | 1.65 | 1.64 |
| Viscosity at 40 C cst | 10.65 | 11.00 | 10.94 | 10.67 |
| Viscosity at 50 C cst | 7.94 | 8.23 | 8.19 | 8.00 |
| Viscosity at 60 C cst | 6.14 | 6.38 | 6.35 | 6.21 |
| Neutralization Number | 0.1 | 0.1 | 0.1 | 0.1 |
| Nickel (ppm) | 41 | 43 | 43 | 42 |
| Vanadium (ppm) | 30 | 30 | 30 | 30 |

TABLE 10

Quality Predictions for Suez Mix '98 Crude Light Distillate Cuts

| Assay Year | 98 | Set 1 IR Only | Set 2 IR & API | Set 3 IR, API & Visc |
|---|---|---|---|---|
| Light Virgin Naphtha (−200 to 160 F) | | | | |
| Volume Yield | 7.8 | 6.8 | 6.9 | 7.1 |
| Benzene (vol %) | 0.3 | 0.5 | 0.5 | 0.6 |
| C5 Isoparaffins (vol %) | 15.5 | 15.6 | 15.6 | 15.5 |
| C6 Isoparaffins (vol %) | 17.9 | 19.2 | 19.0 | 18.8 |
| C7 Isoparaffins (vol %) | 0.1 | 0.5 | 0.5 | 0.6 |
| C5 n-paraffins (vol %) | 18.8 | 20.2 | 20.3 | 20.3 |
| C6 n-paraffins (vol %) | 9.8 | 11.8 | 11.6 | 11.7 |

TABLE 10-continued

Quality Predictions for Suez Mix '98 Crude Light Distillate Cuts

| Assay Year | 98 | Set 1 IR Only | Set 2 IR & API | Set 3 IR, API & Visc |
|---|---|---|---|---|
| Heavy Virgin Naphtha (160 to 360 F) | | | | |
| Volume Yield | 17.1 | 17.0 | 17.1 | 17.1 |
| Sulfur (wt %) | 0.02 | 0.06 | 0.06 | 0.06 |
| API Gravity | 56.4 | 56.0 | 56.0 | 56.0 |
| Benzene (vol %) | 0.6 | 0.6 | 0.6 | 0.6 |
| Naphthenes (vol %) | 38.1 | 36.4 | 36.4 | 36.6 |
| Aromatics (vol %) | 10.8 | 11.9 | 11.9 | 11.9 |
| n-Octanes (vol %) | 5.7 | 5.9 | 5.9 | 5.9 |
| Isooctanes (vol %) | 7.8 | 7.9 | 7.9 | 7.9 |
| C8 Cyclohexanes (vol %) | 3.2 | 2.9 | 2.9 | 2.9 |
| C8 Aromatics (vol %) | 4.0 | 4.3 | 4.3 | 4.2 |
| Kerosene (320 to 500 F) | | | | |
| Volume Yield | 15.6 | 16.5 | 16.4 | 16.5 |
| Sulfur (wt %) | 0.29 | 0.30 | 0.30 | 0.30 |
| API Gravity | 43.5 | 43.2 | 43.2 | 43.2 |
| Pour Point (deg F) | −46 | −53 | −53 | −53 |
| Cloud Point (deg F) | −41 | −44 | −44 | −44 |
| Freeze Point (deg F) | −37 | −39 | −39 | −39 |
| Cetane Index 1990 | 46 | 45 | 45 | 45 |
| Smoke Point | 22 | 23 | 23 | 23 |
| Jet (360 to 530 F) | | | | |
| Volume Yield | 14.7 | 15.7 | 15.6 | 15.6 |
| Sulfur (wt %) | 0.49 | 0.45 | 0.45 | 0.45 |
| API Gravity | 40.8 | 40.7 | 40.7 | 40.7 |
| Pour Point (deg F) | −31 | −36 | −36 | −36 |
| Cloud Point (deg F) | −27 | −28 | −28 | −28 |
| Freeze Point (deg F) | −22 | −23 | −23 | −23 |
| Cetane Index 1990 | 47 | 47 | 47 | 47 |
| Smoke Point | 20 | 21 | 22 | 21 |
| Aromatics (vol %) | 17.0 | 16.1 | 16.2 | 16.2 |
| Viscosity at 40 C cst | 1.74 | 1.74 | 1.74 | 1.74 |
| Viscosity at 100 C cst | 0.83 | 0.84 | 0.84 | 0.85 |
| Viscosity Blending Number 100 C | 0.63 | 0.82 | 0.82 | 0.84 |

TABLE 11

Quality Predictions for Suez Mix '98 Crude Heavy Distillate Cuts

| Assay Year | 98 | Set 1 IR Only | Set 2 IR & API | Set 3 IR, API & Visc |
|---|---|---|---|---|
| Diesel (530 to 650 F) | | | | |
| Volume Yield | 10.310 | 11.150 | 11.100 | 11.110 |
| Sulfur (wt %) | 1.44 | 1.30 | 1.30 | 1.29 |
| Neutralization Number | 0.1 | 0.1 | 0.1 | 0.1 |
| API Gravity | 33.2 | 32.9 | 32.9 | 32.8 |
| Pour Point (deg F) | 33 | 27 | 27 | 27 |
| Cloud Point (deg F) | 33 | 33 | 32 | 32 |
| Cetane Index 1990 | 57 | 56 | 56 | 56 |
| Nitrogen (wt %) | 0.03 | 0.03 | 0.03 | 0.03 |
| Refractive Index (67 C) | 1.4591 | 1.4581 | 1.4582 | 1.4582 |
| Viscosity at 40 C cst | 4.98 | 4.84 | 4.84 | 4.85 |
| Viscosity at 100 C cst | 1.66 | 1.64 | 1.64 | 1.64 |
| Viscosity Blending Number 100 C | 9.43 | 9.33 | 9.33 | 9.33 |

TABLE 11-continued

Quality Predictions for Suez Mix '98 Crude Heavy Distillate Cuts

| Assay Year | 98 | Set 1<br>IR Only | Set 2<br>IR & API | Set 3<br>IR, API & Visc |
|---|---|---|---|---|
| Vacuum Gas Oil (650 to 1050 F) | | | | |
| Volume Yield | 31.3 | 30.8 | 30.7 | 30.6 |
| Sulfur (wt %) | 2.04 | 1.92 | 1.93 | 1.93 |
| Neutralization Number | 0.1 | 0.1 | 0.1 | 0.1 |
| API Gravity | 22.8 | 22.4 | 22.4 | 22.4 |
| Pour Point (deg F) | 112 | 106 | 106 | 106 |
| Nitrogen (wt %) | 0.2 | 0.2 | 0.2 | 0.2 |
| Basic Nitrogen (wt %) | 0.1 | 0.1 | 0.1 | 0.1 |
| Nickel (ppm) | 0.2 | 0.4 | 0.4 | 0.4 |
| Vanadium (ppm) | 0.1 | 0.3 | 0.3 | 0.3 |
| Refractive index (67 C) | 1.4910 | 1.4920 | 1.4920 | 1.4920 |
| Analine Point (deg F) | 184 | 184 | 153 | 153 |
| Conradson Carbon (wt %) | 0.9 | 0.8 | 0.8 | 0.8 |
| Viscosity at 79.4 C cst | 12.57 | 13.08 | 13.10 | 13.16 |
| Viscosity at 100 C cst | 7.36 | 7.55 | 7.55 | 7.58 |
| Viscosity Blending Number 100 C | 21.75 | 21.91 | 21.91 | 21.94 |
| Saturates (wt %) | 49.7 | 50.1 | 50.0 | 49.9 |
| 1-Ring Aromatics (wt %) | 17.2 | 16.7 | 16.8 | 16.8 |
| 2-Ring Aromatics (wt %) | 16.2 | 15.4 | 15.4 | 15.5 |
| 3-Ring Aromatics (wt %) | 6.3 | 7.1 | 7.1 | 7.1 |
| 4-Ring Aromatics (wt %) | 5.8 | 6.1 | 6.1 | 6.2 |
| Polars (wt %) | 4.8 | 4.7 | 4.6 | 4.6 |
| 1-Ring Aromatic Cores (wt %) | 2.8 | 2.7 | 2.7 | 2.7 |
| 2-Ring Aromatic Cores (wt %) | 5.0 | 4.9 | 4.9 | 4.9 |
| 3-Ring Aromatic Cores (wt %) | 3.8 | 3.9 | 3.9 | 3.9 |
| 4-Ring Aromatic Cores (wt %) | 3.0 | 3.2 | 3.2 | 3.2 |
| Polar Cores (wt %) | 2.6 | 2.5 | 2.5 | 2.6 |
| Vacuum Resid (1050 F+) | | | | |
| Volume Yield | 18.9 | 18.5 | 18.6 | 18.5 |
| Sulfur (wt %) | 3.6 | 3.6 | 3.6 | 3.6 |
| Neutralization Number | 0.0 | 0.3 | 0.3 | 0.3 |
| API Gravity | 3.9 | 4.9 | 4.9 | 4.9 |
| Pour Point (deg F) | 192.6 | 164.4 | 163.6 | 162.3 |
| Nitrogen (wt %) | 0.5 | 0.8 | 0.8 | 0.8 |
| Retractive index (67 C) | 1.5 | 1.5 | 1.5 | 1.5 |
| Analine Point (deg F) | 198.2 | 195.7 | 195.5 | 195.3 |
| Mean Average Boiling Point (deg F) | 1249.0 | 1249.0 | 1249.0 | 1249.0 |
| Conradson Carbon (wt %) | 24.3 | 25.2 | 25.3 | 25.3 |
| Viscosity at 79.4 C cst | 99100.0 | 10900.0 | 10900.0 | 11100.0 |
| Viscosity at 100 C cst | 12200.0 | 12900.0 | 13000.0 | 13000.0 |
| Viscosity Blending Number 100 C | 43.6 | 43.7 | 43.7 | 43.7 |
| Viscosity at 135 C cst | 940.0 | 959.0 | 961.4 | 962.3 |

TABLE 12

Analysis of Escravos '99

| Crude | Assay Year | Country | Region | Nearness Index | Set 1<br>IR Only<br>Entire Library | Set 2<br>IR & API<br>Entire Library | Set 3<br>IR, API & Visc<br>Entire Library | Set 4<br>IR, API & Visc<br>African Crudes |
|---|---|---|---|---|---|---|---|---|
| BINTULU | 98 | MALAYSIA | FAREAST | 198 | 2.1 | 2.2 | 2.2 | |
| BINTULU CONDENSATE | 99 | MALAYSIA | FAREAST | 268 | | 0.1 | 0.1 | |
| BRASS RIVER | 99 | NIGERIA | AFRICA | 66 | | | | 23.1 |
| BUNGA KEKWA | 97 | MALAYSIA | FAREAST | 233 | 3.5 | 3.3 | 3.3 | |
| CHALLIS | 98 | AUSTRALIA | FAREAST | 95 | 5.0 | 5.0 | 5.1 | |
| ERHA | 99 | NIGERIA | AFRICA | 2 | | | | 12.3 |
| EZZAOUIA | 00 | TUNISIA | AFRICA | 238 | | | | 11.1 |
| GRYPHON | 98 | U.K. | EUROPE | 294 | 0.9 | 0.8 | 0.8 | |
| KUMKOL | 99 | RUSSIA | FSU | 245 | 9.2 | 9.4 | 9.3 | |
| LION | 00 | IVORYCOAST | AFRICA | 102 | | | | 3.6 |
| LIUHUA | 98 | CHINA | FAREAST | 228 | 3.8 | 3.6 | 3.5 | |
| LOKELE | 96 | CAMEROON | AFRICA | 289 | 3.0 | 2.8 | 2.8 | 6.1 |
| MOUDI | 99 | CAMEROON | AFRICA | 36 | 8.8 | 9.4 | 9.4 | |
| NIGERIAN LIGHT (BONNY | 00 | NIGERIA | AFRICA | 3 | 1.2 | 0.7 | 0.9 | 16.1 |
| NIGERIAN MEDIUM | 98 | NIGERIA | AFRICA | 50 | 14.6 | 15.2 | 15.1 | 12.2 |
| NORNE | 97 | NORWAY | EUROPE | 38 | 4.5 | 5.0 | 5.0 | |

TABLE 12-continued

Analysis of Escravos '99

| Crude | Assay Year | Country | Region | Nearness Index | Set 1 IR Only Entire Library | Set 2 IR & API Entire Library | Set 3 IR, API & Visc Entire Library | Set 4 IR, API & Visc African Crudes |
|---|---|---|---|---|---|---|---|---|
| ODUDU BLEND | 96 | NIGERIA | AFRICA | 187 | 17.5 | 18.2 | 18.1 | 11.3 |
| ORQUIDEA | 99 | ANGOLA | AFRICA | 290 | | | | 3.3 |
| PENNINGTON | 99 | NIGERIA | AFRICA | 18 | 10.6 | 8.8 | 8.8 | |
| QARUN | 99 | EGYPT | AFRICA | 191 | | | | 0.9 |
| RUBY | 99 | VIETNAM | FAREAST | 112 | 2.4 | 2.3 | 2.2 | |
| SABLE ISLAND | 00 | CANADA | CANADA | 271 | 3.5 | 3.4 | 3.5 | |
| SHAYBAH | 97 | S.ARABIA | MIDEAST | 149 | 2.2 | 2.0 | 2.0 | |
| SHARJAH COND | 98 | SHARJAH | MIDEAST | 282 | 1.7 | 1.6 | 1.0 | |
| SHARJAH COND | 99 | SHARJAH | MIDEAST | 287 | | | 0.6 | |
| STAG | 98 | AUSTRALIA | FAREAST | 97 | 0.1 | | | |
| TAPIS | 98 | MALAYSIA | FAREAST | 206 | 3.7 | 4.8 | 4.8 | |
| WEST TEXAS SOUR | 99 | TEXAS | U.S.A. | 135 | 1.4 | 1.4 | 1.4 | |
| Fit R-squared | | | | | 0.9997 | 0.9997 | 0.9997 | 0.9994 |
| API (Predicted - Actual) | | | | | | -0.1 | -0.1 | 0.0 |
| Visc40C (Predicted - Actual) | | | | | | | 0.00 | 0.02 |

For the columns labeled Sets 1–3, this spectrum was fit to the remaining 296 crude spectra in the database. All 3 fits had $R^2$ values greater than 0.9997. This example demonstrates how the current invention might be used to analyze an unknown crude when no previous sample of that crude is present in the database. No previous Escravos sample is represented in the database, and no single crude contributes more than 25% of the "Virtual Blend". Despite this, the predictions shown in Table 13–15 are quite reasonable, mostly within the reproducibility of the assay data.

TABLE 13

Whole Crude Quality Predictions for Escravos '99

| Assay Year | 1999 | Set 1 IR Only Entire Library | Set 2 IR & API Entire Library | Set 3 IR, API & Visc Entire Library | Set 4 IR, API & Visc African Crudes |
|---|---|---|---|---|---|
| WHOLE CRUDE PROPERTIES | | | | | |
| API Gravity | 33.4 | 33.2 | 33.3 | 33.3 | 33.3 |
| Specific Gravity | 0.8584 | 0.8592 | 0.8588 | 0.8587 | 0.8585 |
| Conradson Carbon (wt %) | 1.5 | 1.8 | 1.8 | 1.8 | 1.6 |
| Nitrogen (wt %) | 0.13 | 0.11 | 0.11 | 0.11 | 0.12 |
| Sulfur (wt %) | 0.21 | 0.20 | 0.20 | 0.20 | 0.21 |
| Viscosity at 40 C cst | 4.91 | 4.95 | 4.92 | 4.91 | 4.93 |
| Viscosity at 50 C cst | 3.84 | 3.97 | 3.95 | 3.94 | 3.97 |
| Viscosity at 60 C cst | 3.11 | 3.27 | 3.25 | 3.25 | 3.28 |
| Neutralization Number | 0.7 | 0.6 | 0.5 | 0.5 | 0.6 |
| Nickel (ppm) | 4.9 | 5.6 | 5.6 | 5.6 | 5.6 |
| Vanadium (ppm) | 0.5 | 0.9 | 0.9 | 0.9 | 0.8 |

TABLE 14

Quality Predictions for Escravos '99 Crude Light Distillate Cuts

| Assay Year | | Set 1 IR Only Entire Library | Set 2 IR & API Entire Library | Set 3 IR, API & Visc Entire Library | Set 4 IR, API & Visc African Crudes |
|---|---|---|---|---|---|
| Light Virgin Naphtha (-200 to 160 F) | | | | | |
| Volume Yield | 5.6 | 5.6 | 5.7 | 5.7 | 6.0 |
| Benzene (vol %) | 1.0 | 1.1 | 1.1 | 1.1 | 1.0 |
| C5 Isoparaffins (vol %) | 14.6 | 18.5 | 18.6 | 18.4 | 16.2 |
| C6 Isoparaffins (vol %) | 19.3 | 20.2 | 20.2 | 20.2 | 20.7 |
| C7 Isoparaffins (vol %) | 0.1 | 0.1 | 0.1 | 0.1 | 0.1 |
| C5 n-paraffins (vol %) | 15.4 | 17.3 | 17.2 | 17.1 | 15.8 |
| C6 n-paraffins (vol %) | 11.5 | 11.0 | 10.9 | 10.9 | 11.1 |

TABLE 14-continued

Quality Predictions for Escravos '99 Crude Light Distillate Cuts

| Assay Year | Set 1<br>IR Only<br>Entire<br>Library | Set 2<br>IR & API<br>Entire<br>Library | Set 3<br>IR, API & Visc<br>Entire<br>Library | Set 4<br>IR, API & Visc<br>African<br>Crudes |
|---|---|---|---|---|
| Heavy Virgin Naphtha (160 to 360 F) | | | | |
| Volume Yield | 19.4 | 19.1 | 19.2 | 19.2 | 19.1 |
| Sulfur (wt %) | 0.01 | 0.01 | 0.01 | 0.01 | 0.01 |
| API Gravity | 52.5 | 52.5 | 52.6 | 52.6 | 53.2 |
| Benzene (vol %) | 0.6 | 0.7 | 0.7 | 0.7 | 0.7 |
| Naphthenes (vol %) | 46.1 | 45.4 | 45.4 | 45.4 | 45.0 |
| Aromatics (vol %) | 14.1 | 14.8 | 14.7 | 14.7 | 13.4 |
| n-Octanes (vol %) | 5.0 | 4.7 | 4.7 | 4.7 | 5.0 |
| Isooctanes (vol %) | 7.1 | 7.3 | 7.4 | 7.4 | 7.8 |
| C8 Cyclohexanes (vol %) | 5.5 | 4.5 | 4.5 | 4.5 | 4.5 |
| C8 Aromatics (vol %) | 6.4 | 6.0 | 6.0 | 6.0 | 5.8 |
| Kerosene (320 to 500 F) | | | | |
| Volume Yield | 21.1 | 21.3 | 21.3 | 21.3 | 20.3 |
| Sulfur (wt %) | 0.04 | 0.04 | 0.04 | 0.04 | 0.04 |
| API Gravity | 39.8 | 39.4 | 39.5 | 39.5 | 39.7 |
| Pour Point (deg F) | −62 | −71 | −71 | −71 | −72 |
| Cloud Point (deg F) | −55 | −54 | −54 | −54 | −54 |
| Freeze Point (deg F) | −49 | −50 | −50 | −50 | −49 |
| Cetane Index 1990 | 39 | 39 | 39 | 39 | 40 |
| Smoke Point | 18 | 19 | 19 | 19 | 19 |
| Jet (360 to 530 F) | | | | |
| Volume Yield | 20.9 | 21.8 | 21.8 | 21.8 | 20.7 |
| Sulfur (wt %) | 0.06 | 0.06 | 0.06 | 0.06 | 0.05 |
| API Gravity | 37.1 | 36.9 | 36.9 | 36.9 | 37.1 |
| Pour Point (deg F) | −46 | −55 | −55 | −55 | −57 |
| Cloud Point (deg F) | −39 | −38 | −38 | −38 | −38 |
| Freeze Point (deg F) | −32 | −34 | −34 | −34 | −33 |
| Cetane Index 1990 | 41 | 41 | 41 | 41 | 41 |
| Smoke Point | 17 | 17 | 17 | 17 | 17 |
| Aromatics (vol %) | 18.20 | 17.33 | 17.48 | 17.49 | 17.86 |
| Viscosity at 40 C cst | 1.91 | 1.95 | 1.94 | 1.94 | 1.94 |
| Viscosity at 100 C cst | 0.89 | 0.90 | 0.90 | 0.90 | 0.90 |
| Viscosity Blending Number 100 C | 1.58 | 1.75 | 1.74 | 1.73 | 1.74 |

TABLE 15

Quality Predictions for Escravos '99 Crude Heavy Distillate Cuts

| Assay Year | 1999 | Set 1<br>IR Only<br>Entire<br>Library | Set 2<br>IR & API<br>Entire<br>Library | Set 3<br>IR, API & Visc<br>Entire<br>Library | Set 4<br>IR, API & Visc<br>African<br>Crudes |
|---|---|---|---|---|---|
| Diesel (530 to 650 F) | | | | | |
| Volume Yield | 16.4 | 16.0 | 15.9 | 15.9 | 16.4 |
| Sulfur (wt %) | 0.18 | 0.17 | 0.17 | 0.17 | 0.17 |
| Neutralization Number | 0.4 | 0.5 | 0.5 | 0.5 | 0.5 |
| API Gravity | 30.4 | 30.7 | 30.7 | 30.7 | 30.4 |
| Pour Point (deg F) | 18 | 9 | 10 | 10 | 10 |
| Cloud Point (deg F) | 26 | 25 | 25 | 25 | 27 |
| Cetane Index 1990 | 50 | 51 | 51 | 51 | 50 |
| Nitrogen (wt %) | 0.01 | 0.01 | 0.01 | 0.01 | 0.02 |
| Refractive Index (67 C) | 1.4620 | 1.4837 | 1.4637 | 1.4637 | 1.4649 |
| Viscosity at 40 C cst | 5.61 | 5.73 | 5.72 | 5.72 | 5.79 |
| Viscosity at 100 C cst | 1.76 | 1.78 | 1.77 | 1.77 | 1.78 |
| Viscosity Blending Number 100 C | 10.06 | 10.17 | 10.16 | 10.16 | 10.19 |
| Vacuum Gas Oil (650 to 1050 F) | | | | | |
| Volume Yield | 29.7 | 30.0 | 30.0 | 30.0 | 30.5 |
| Sulfur (wt %) | 0.30 | 0.30 | 0.30 | 0.30 | 0.31 |
| Neutralization Number | 1.1 | 1.0 | 1.0 | 1.0 | 1.0 |
| API Gravity | 22.3 | 22.0 | 22.1 | 22.1 | 21.7 |
| Pour Point (deg F) | 104 | 87 | 87 | 87 | 90 |
| Nitrogen (wt %) | 0.15 | 0.15 | 0.15 | 0.15 | 0.15 |
| Basic Nitrogen (wt %) | 0.07 | 0.06 | 0.06 | 0.06 | 0.07 |

TABLE 15-continued

Quality Predictions for Escravos '99 Crude Heavy Distillate Cuts

| Assay Year | 1999 | Set 1<br>IR Only<br>Entire<br>Library | Set 2<br>IR & API<br>Entire<br>Library | Set 3<br>IR, API & Visc<br>Entire<br>Library | Set 4<br>IR, API & Visc<br>African<br>Crudes |
|---|---|---|---|---|---|
| Nickel (ppm) | 0.1 | 0.2 | 0.2 | 0.2 | 0.2 |
| Vanadium (ppm) | 0.0 | 0.0 | 0.0 | 0.0 | 0.0 |
| Refractive Index (67 C) | 1.4900 | 1.4910 | 1.4910 | 1.4910 | 1.4930 |
| Analine Point (deg F) | 181.3 | 178.6 | 178.6 | 178.6 | 177.9 |
| Conradson Carbon (wt %) | 0.4 | 0.5 | 0.5 | 0.5 | 0.5 |
| Viscosity at 79.4 C cst | 13.10 | 14.10 | 14.08 | 14.07 | 14.35 |
| Viscosity at 100 C cst | 7.43 | 7.84 | 7.82 | 7.82 | 7.93 |
| Viscosity Blending Number 100 C | 21.81 | 22.14 | 22.13 | 22.13 | 22.21 |
| Saturates (wt %) | 53.8 | 56.0 | 56.0 | 56.1 | 54.4 |
| 1-Ring Aromatics (wt %) | 18.0 | 15.4 | 15.3 | 15.3 | 16.0 |
| 2-Ring Aromatics (wt %) | 13.3 | 13.0 | 13.0 | 13.0 | 13.4 |
| 3-Ring Aromatics (wt %) | 6.2 | 6.1 | 6.1 | 6.1 | 6.3 |
| 4-Ring Aromatics (wt %) | 5.1 | 5.2 | 5.2 | 5.2 | 5.5 |
| Polars (wt %) | 3.8 | 4.3 | 4.3 | 4.3 | 4.5 |
| 1-Ring Aromatic Cores (wt %) | 3.2 | 3.0 | 3.0 | 3.0 | 3.1 |
| 2-Ring Aromatic Cores (wt %) | 5.4 | 5.3 | 5.3 | 5.3 | 5.5 |
| 3-Ring Aromatic Cores (wt %) | 3.3 | 3.2 | 3.2 | 3.2 | 3.4 |
| 4-Ring Aromatic Cores (wt %) | 2.4 | 2.2 | 2.1 | 2.1 | 2.4 |
| Polar Cores (wt %) | 1.1 | 1.6 | 1.6 | 1.6 | 1.4 |
| Vacuum Resid (1050 F+) | | | | | |
| Volume Yield | 8.0 | 7.6 | 7.5 | 7.5 | 7.3 |
| Sulfur (wt %) | 0.45 | 0.59 | 0.59 | 0.59 | 0.64 |
| Neutralization Number | 1.2 | 0.8 | 0.8 | 0.8 | 1.0 |
| API Gravity | 12.0 | 8.5 | 8.4 | 8.4 | 9.1 |

The Escravos example further demonstrates the significant difference between the methodology of the current invention and that described by B. Descales, D. Lambert, J. LLinas, A. Martens, S. Osta, M. Sanchez and S. Bages (U.S. Pat. No. 6,070,128 May 30, 2000). Euclidean distances between the 296 corrected reference spectra and the corrected spectrum of the Escravos sample were calculated, and the samples were ranked in terms of increasing distance. The results are shown in the column labeled "nearness index" in Table 12. The most significant crudes in the fit are not those with the "closest" spectrum to that being analyzed. The nearest neighbor to Escravos, a Odudu Blend assayed in 2000, is not included in any of the fits. The second and third "closest" samples represent less than 2% of the fit unless the components are restricted to a subset of African crudes, and the fourth through seventeenth "closest" samples are not included in the fits. The methodology of the current invention is clearly capable of selecting from a diverse set of crudes those whose combination best matches the compositional information inherent in the infrared spectra. The current invention can fit spectra and predict qualities even for materials that do not have a close "nearest neighbor" spectrum in the database.

The Escravos example further illustrates how the method of this invention can be used to infer information about the sample being analyzed. When analyzed with the entire library, crudes from Africa account for over 50% of the fit components. In fact, the Escravos data can be adequately fit using a subset consisting of only African crudes. This sort of analysis can be used to infer a region from which a crude sample originates.

The inclusion of inspection data such as API Gravity and viscosity has subtle effects on the predicted Virtual Blends. The inclusion of such data has been found to improve the prediction of distillation yields. This improvement is demonstrated in Table 16.

TABLE 16

Prediction Errors for Fits Using Various Combinations of IR and Inspection Data

| | Inspections | | | |
|---|---|---|---|---|
| | Cut FBP<br>Deg. F. | API<br>Visc 40 C | API | None |
| API | | 0.32 | 0.30 | 0.58 |
| Visc (40 C) | | 3.70 | 7.56 | 7.91 |
| Cut# | | | | |
| 1 | 158 | 0.82 | 0.81 | 0.93 |
| 2 | 212 | 0.94 | 0.93 | 1.16 |
| 3 | 257 | 0.93 | 0.90 | 1.25 |
| 4 | 302 | 0.96 | 0.93 | 1.34 |
| 5 | 347 | 0.98 | 0.96 | 1.42 |
| 6 | 401 | 1.04 | 1.04 | 1.50 |
| 7 | 428 | 1.09 | 1.10 | 1.54 |
| 8 | 455 | 1.13 | 1.15 | 1.57 |
| 9 | 509 | 1.18 | 1.21 | 1.58 |
| 10 | 563 | 1.18 | 1.24 | 1.57 |
| 11 | 606 | 1.13 | 1.24 | 1.53 |
| 12 | 650 | 1.05 | 1.20 | 1.46 |
| 13 | 702 | 0.98 | 1.15 | 1.38 |
| 14 | 727 | 0.97 | 1.13 | 1.34 |
| 15 | 752 | 0.95 | 1.12 | 1.31 |
| 16 | 777 | 0.95 | 1.11 | 1.29 |
| 17 | 802 | 0.95 | 1.11 | 1.26 |
| 18 | 828 | 0.95 | 1.11 | 1.24 |
| 19 | 853 | 0.96 | 1.11 | 1.22 |
| 20 | 878 | 0.97 | 1.12 | 1.21 |
| 21 | 903 | 0.98 | 1.12 | 1.19 |
| 22 | 928 | 0.98 | 1.11 | 1.17 |
| 23 | 954 | 0.97 | 1.10 | 1.14 |
| 24 | 979 | 0.96 | 1.07 | 1.10 |
| 25 | 1004 | 0.94 | 1.04 | 1.06 |
| 26 | 1029 | 0.92 | 1.01 | 1.02 |
| 27 | 1054 | 0.90 | 0.98 | 0.99 |
| RMS Dist | | 0.99 | 1.08 | 1.30 |

TABLE 16-continued

Prediction Errors for Fits Using Various Combinations of IR and Inspection Data

|  | Inspections | | | |
| --- | --- | --- | --- | --- |
|  | Cut FBP Deg. F. | API Visc 40 C | API | None |
| Sulfur |  | 0.19 | 0.19 | 0.19 |
| Nitrogen |  | 0.03 | 0.03 | 0.03 |
| Neutralization Number |  | 0.10 | 0.10 | 0.10 |

The standard error for the prediction of cumulative yields and key qualities is shown for fits of the 161 crudes with the $R^2$ values greater than 0.9992 from the cross validation alysis. The root mean square (RMS) error in the cumulative yield predictions for fits calculated with API Gravity, or with the combination of API Gravity and viscosity at 40° C. are significantly better than those calculated with the IR spectra alone. The calculated API Gravity and viscosity numbers for fits that include them are also improved relative to the prediction based on IR. For compositional type predictions (sulfur, nitrogen or neutralization number), the inclusion of the inspections has minimal affect.

Other types of inspection data can be utilized by this invention. Examples of such data include, but are not limited to weight percentage of sulfur in material, or percentage of the material distilled at certain fixed temperatures as estimated by gas chromatographic simulated distillation.

An additional example demonstrates that the method of the current invention can be applied for the detailed analysis of materials other than crude oil. The method can be used to predict molecular distribution and Structure-Oriented Lumping (SOL) information for feeds to catalytic cracking units. The molecular distribution information predicted is dependent on the specific reference analysis employed and includes information such as paraffin, naphthene and aromatic molecular types as a function of boiling range. Structured-Oriented Lumping is described by Quann and Jaffe (*Ind. Eng. Chem. Res.* 1992, 31, 2483–2497), as is its use in process modeling (*Chemical Engineering Science*, 1996, 51, 1615–1635). For this example, the references consist of 49 virgin gas oils and process streams that are components typically used as feeds to a fluid catalytic cracking process. The references have been analyzed via High-Detail Hydrocarbon Analysis (HDHA) method described by Jacob, Quann, Sanchez and Wells (*Oil and Gas Journal*, Jul. 6, 1998) to provide the SOL information. FT-MIR Spectra of these materials were obtained at 60° C., using cells with $CaF_2$ windows and a nominal pathlength of 0.5 millimeter. Data in the 5524.1 to 3120.3 $cm^{-1}$, 2699.9 to 2384.5 $cm^{-1}$, and 2290.1 to 1679.7 $cm^{-1}$ region were used in the analysis. Two sets of quadratic polynomials spanning the range from 5524.1 to 3120.3 $cm^{-1}$ and from, 2699.9 to 1679.7 $cm^{-1}$ were used to correct for baseline variation. A liquid water correction was generated as was previously described. 26 spectra of catfeeds to which water was added were collected. Difference spectra were generated by subtracting spectra of the corresponding dry catfeeds. The difference spectra were orthogonalized to the polynomial corrections. A singular value decomposition on the resulting data was conducted, and two liquid water correction vectors were retained. An additional correction vector for water vapor was also generated as previously described. Ten water vapor spectra were orthogonalized to the polynomials and the liquid water corrections. A singular value decomposition of the resulting data was conducted, and one water vapor correction was retained. For this example, no inspection data was employed.

To demonstrate the prediction of SOL information, selected samples from the 49 catfeeds were removed from the database and analyzed relative to the remaining 48 samples as if they were unknowns. Table 17 shows the fit $R^2$ values and calculated blend compositions for three catfeed samples.

TABLE 17

Analyses of Catfeeds

|  | Quatar Marine 559–990 F | Fosterton Blend 567–1003 F | Arab Super Light 568–1015 F |
| --- | --- | --- | --- |
| R2 | 0.99994 | 0.99983 | 0.99963 |
| Torrence Feed |  |  | 2.58 |
| MCB | 0.13 | 0.47 |  |
| Paulsboro Feed |  | 1.67 |  |
| Bach Ho VGO |  |  | 4.19 |
| Abu Safah VGO | 3.87 |  |  |
| Arabian Medium VGO | 5.04 | 7.94 |  |
| Olmeca 300 N Extract | 1.89 |  |  |
| Arabian Light VGO | 4.26 | 21.53 |  |
| Kuwait VGO | 60.14 |  |  |
| Ebome VGO | 3.44 |  | 28.17 |
| LLoyd Kerrobert Kerosene |  | 9.64 |  |
| Bow River VGO |  | 48.05 |  |
| Light Soure Blend VGO | 6.00 | 1.99 |  |
| Cooper Basin VGO |  |  | 10.90 |
| OCS VGO |  | 6.02 |  |
| Edmonton Mixed Sour Oil VGO |  | 0.27 |  |
| Fosterton VGO | 6.14 |  |  |
| Olmeca 100 N Extract |  | 2.11 |  |
| Olmeca 100 N Raffinate |  |  | 44.24 |
| Jurong Feed |  | 0.31 |  |
| Azeri Light VGO |  |  | 2.84 |
| Heidrun VGO | 0.02 |  | 7.09 |
| Anasuria VGO | 9.08 |  |  |

The "Virtual Blends" shown in Table 17 are used to calculate SOL information as shown in Table 18.

TABLE 18

SOL Lump (Moles Group per Kilogram) Predicted vs. Actual

|  | Quatar Marine | | Fosterton Blend | | Arab Super Light | |
| --- | --- | --- | --- | --- | --- | --- |
|  | 559-990F Actual | Predicted | 567-1003F Actual | Predicted | 568-1015F Actual | Predicted |
| A6 | 1.94 | 1.95 | 2.31 | 2.13 | 0.79 | 0.96 |
| A4 | 0.77 | 0.77 | 1.02 | 0.96 | 0.56 | 0.46 |
| A2 | 0.02 | 0.02 | 0.02 | 0.03 | 0.01 | 0.01 |
| N6 | 0.91 | 0.85 | 0.94 | 0.98 | 1.43 | 1.21 |
| N5 | 0.02 | 0.03 | 0.05 | 0.04 | 0.00 | 0.01 |
| N4 | 1.50 | 1.57 | 1.85 | 2.12 | 1.66 | 1.72 |
| N3 | 0.31 | 0.37 | 0.39 | 0.37 | 0.00 | 0.04 |
| N2 | 0.02 | 0.03 | 0.04 | 0.04 | 0.02 | 0.02 |
| N1 | 0.50 | 0.46 | 0.61 | 0.54 | 0.06 | 0.11 |
| R | 44.14 | 44.01 | 38.91 | 39.11 | 49.65 | 49.85 |
| br | 1.95 | 1.90 | 1.71 | 1.74 | 2.38 | 2.03 |
| me | 4.51 | 4.58 | 5.33 | 5.41 | 3.81 | 3.68 |
| H | 0.52 | 0.41 | 0.14 | 0.13 | 1.00 | 1.04 |
| A_A | 0.59 | 0.57 | 0.74 | 0.67 | 0.15 | 0.19 |
| S | 0.71 | 0.73 | 0.87 | 0.80 | 0.02 | 0.11 |
| AN | 0.01 | 0.01 | 0.03 | 0.02 | 0.00 | 0.01 |
| NN | 0.08 | 0.09 | 0.14 | 0.10 | 0.01 | 0.01 |

The "Virtual Blends" can also be used to predict chemical and physical properties of the feeds as shown in Table 19.

TABLE 19

Chemical and Physical Properties for Catfeeds, Predicted vs. Actual

|  |  | Quatar Marine | | Fosterton Blend | | Arab Super Light | |
|---|---|---|---|---|---|---|---|
|  |  | Actual | Pred | Actual | Pred | Actual | Pred |
| Gravity | API | 24.3 | 23.7 | 19.6 | 19.6 | 31.9 | 31.5 |
| Density at 70C | G/CC | 0.8720 | 0.8754 | 0.9004 | 0.9007 | 0.8286 | 0.8310 |
| Molecular Weight |  | 323 | 332 | 326 | 339 | 322 | 325 |
| Refractive Index 70C | RI70 | 1.4912 | 1.4926 | 1.5063 | 1.5041 | 1.4630 | 1.4647 |
| Aniline Point | DEGF | 170 | 171 | 157 | 160 | 189 | 190 |
| Hydrogen | WT % | 12.2 | 12.2 | 11.6 | 11.8 | 13.5 | 13.4 |
| Sulfur | WT % | 2.3 | 2.3 | 2.8 | 2.6 | 0.1 | 0.3 |
| Aliphatic Sulfur | WT % | 0.4 | 0.5 | 0.8 | 0.7 | 0.0 | 0.1 |
| Aromatic Sulfur | WT % | 1.8 | 1.9 | 2.0 | 1.9 | 0.0 | 0.2 |
| Thiophene Index |  | 12 | 12 | 11 | 12 | 13 | 13 |
| Nitrogen | PPMW | 1252 | 1388 | 2331 | 1688 | 167 | 247 |
| Basic Nitrogen | PPMW | 178 | 189 | 385 | 343 | 34 | 82 |
| Aromatic Carbon (Ca) | % | 20.7 | 20.8 | 25.4 | 23.5 | 9.7 | 10.6 |
| KV at 130F | CS | 13.63 | 15.26 | 18.83 | 22.29 | 9.69 | 9.84 |
| KV at 100C | CS | 4.31 | 4.67 | 5.31 | 6.00 | 3.48 | 3.51 |
| Total P/N/A | WT % |  |  |  |  |  |  |
| Total Paraffins |  | 24.9 | 24.1 | 14.5 | 14.2 | 31.4 | 35.2 |
| Total Naphthenes |  | 26.8 | 25.7 | 26.3 | 28.7 | 47.9 | 40.1 |
| Total Aromatics |  | 48.3 | 50.2 | 59.2 | 57.2 | 20.7 | 24.6 |
| HPLC-2 Analysis | WT % |  |  |  |  |  |  |
| Saturates |  | 51.7 | 49.8 | 40.8 | 42.8 | 79.3 | 75.4 |
| Arc 1 |  | 16.2 | 15.9 | 17.3 | 17.4 | 8.3 | 12.0 |
| Arc 2 |  | 14.8 | 16.6 | 19.8 | 18.3 | 5.9 | 6.8 |
| Arc 3 |  | 8.8 | 8.7 | 9.6 | 10.1 | 3.9 | 3.5 |
| Arc 4 |  | 7.8 | 8.2 | 10.9 | 9.9 | 2.4 | 2.0 |
| Polars |  | 0.6 | 0.8 | 1.5 | 1.5 | 0.2 | 0.3 |
| Sim Dist M1567 (9 Pts) | DEGF |  |  |  |  |  |  |
| IBP |  | 539 | 545 | 525 | 544 | 546 | 523 |
| 5% Off |  | 577 | 593 | 586 | 594 | 576 | 582 |
| 10% Off |  | 598 | 615 | 611 | 619 | 589 | 610 |
| 30% Off |  | 675 | 693 | 695 | 707 | 644 | 689 |
| 50% Off |  | 753 | 766 | 773 | 778 | 713 | 731 |
| 70% Off |  | 834 | 842 | 853 | 857 | 792 | 774 |
| 90% Off |  | 919 | 926 | 940 | 976 | 907 | 853 |
| 95% Off |  | 949 | 959 | 973 | 1047 | 952 | 904 |
| EP |  | 1010 | 1033 | 1039 | 1164 | 1028 | 1009 |

The current invention is shown to be capable of predicting properties of the whole material (e.g. whole crude), and of subfractions of the material (e.g. distillate cuts). The current invention can predict qualities that are volumetrically blendable (e.g. volume % yield), gravimetrically blendable (e.g. elemental compositions), or nonlinearly blendable (e.g cold flow properties). The current invention can make such predictions based solely on spectral data, but some predictions may be improved by including inspection data in the calculation.

What is claimed is:

1. A method for determining an assay property of an unknown material comprising:
   (a) determining multivariate analytical data of said unknown material,
   (b) fitting said multivariate analytical data to a linear combination of known multivariate analytical data in a database to determine the coefficients of the linear combination, wherein said database includes multivariate analytical data of reference materials whose assay properties are known, and
   (c) determining said assay property of said unknown material from the coefficients and assay properties of said reference materials.

2. The method of claim 1 further comprising the step of eliminating signals from the multivariate analytical data of said unknown material and said reference materials that are not related to the molecular constituents of the materials.

3. The method of claim 1 further comprising the step of augmenting said multivariate analytical data with inspection data to form augmented data such that said augmented data of the unknown material is fit as a linear combination of multivariate analytical data augmented with inspection data of the known reference materials.

4. The method of claim 1 further comprising the steps of eliminating signals from the multivariate analytical data that are not related to the molecular constituents of the material, and augmenting said multivariate analytical data with inspection data to form augmented data such that said augmented data of the unknown material is fit to a linear combination of multivariate analytical data augmented with inspection data of the known reference materials.

5. The method of claim 2, wherein said step of eliminating signals is performed by orthogonalizing the multivariate analytical data of the reference and unknown materials to example data of the signals to be eliminated.

6. The method of claim 1 wherein said step of fitting said multivariate analytical data is determined using a non-negative least squares algorithm.

7. The method of claim 4 wherein said step of eliminating signals is performed by orthogonalizing the multivariate analytical data of the reference and unknown materials to example data of the signals to be eliminated.

8. The method of claim 2 wherein said step of fitting said multivariate analytical data is determined using a non-negative least squares algorithm.

9. The method of claim 3 wherein said step of fitting said multivariate analytical data is determined using a non-negative least squares algorithm.

10. The method of claim 4 wherein said step of fitting said multivariate analytical data is determined using a non-negative least squares algorithm.

11. The method of claim 5 wherein said step of fitting said multivariate analytical data is determined using a non-negative least squares algorithm.

12. The method of claim 7 wherein said step of fitting said multivariate analytical data is determined using a non-negative least squares algorithm.

13. The method as in any one of claims 1–6 or 7–12, wherein said multivariate analytical data is a spectrum.

14. The method as in any one of claims 1–6 or 7–12, wherein said spectrum is an IR spectrum.

15. The method as in any one of claims 1–6 or 7–12, wherein said multivariate analytical data is a chromatogram.

16. The method as in claims 3, 4, 9, or 10, wherein said inspection data is in volumetrically blendable form.

17. The method as in claims 3, 4, 9, or 10 wherein said inspection data is API or specific gravity.

18. The method as in claims 3, 4, 9 or 10 wherein said inspection data is viscosity.

19. The method as in claims 3, 4, 9 or 10 wherein said inspection data is API or specific gravity and viscosity.

20. The method as in any one of claims 1–6 or 7–12, wherein said assay properties are chemical, physical and performance properties of the material or subfractions thereof.

21. The method claim 20 wherein said unknown material is crude oil and said assay property is any physical, chemical or performance property of the whole crude or any distillation cut thereof.

22. The method of claim 21 wherein said assay property is a physical property.

23. The method of claim 22 wherein said physical property is distillation yields.

24. The method of claim 22 wherein said physical property is a cold flow property.

25. The method of claim 24 wherein said cold flow property is freeze point.

26. The method of claim 24 wherein said cold flow property is cloud point.

27. The method of claim 24 wherein said cold flow property is pour point.

28. The method of claim 21 wherein said assay property is a chemical property.

29. The method of claim 28 wherein said chemical property is elemental composition.

30. The method of claim 29 wherein said elemental composition is sulfur content.

31. The method of claim 29 wherein said elemental composition is nitrogen content.

32. The met method of claim 28 wherein said chemical property is molecular composition.

33. The method of claim 32 wherein said molecular composition is saturates content.

34. The method of claim 32 wherein said molecular composition is aromatics content.

35. The method of claim 32 wherein said molecular composition is aromatic ring distribution.

36. The method of claim 21 wherein said assay property is a performance property.

37. The method of claim 36 wherein said performance property is octane number.

38. The method of claim 36 wherein said performance property is cetane number.

39. The method of claim 21 wherein said property is a whole crude property.

40. The method of claim 21 wherein said property is a distributed property.

41. The method claim 20 wherein said unknown material is a feed to or product from a process unit and said assay property is any physical, chemical or performance property of the feed or any subfraction thereof.

42. The method of claim 41 wherein said assay property is a physical property.

43. The method of claim 42 wherein said physical property is distillation yield.

44. The method of claim 41 wherein said assay property is a chemical property.

45. The method of claim 44 wherein said chemical property is elemental composition.

46. The method of claim 45 wherein said elemental composition is sulfur content.

47. The method of claim 45 wherein said elemental composition is nitrogen content.

48. The method of claim 45 wherein said elemental composition is aromatic carbon content.

49. The method of claim 44 wherein said chemical property is molecular composition.

50. The method of claim 49 wherein said molecular composition is saturates content.

51. The method of claim 50 wherein said molecular composition is a function of boiling point.

52. The method of claim 49 wherein said molecular composition is paraffins content.

53. The method of claim 52 wherein said molecular composition is a function of boiling point.

54. The method of claim 49 wherein said molecular composition is naphthenes content.

55. The method of claim 54 wherein said molecular composition is a function of boiling point.

56. The method of claim 49 wherein said molecular composition is aromatics content.

57. The method of claim 56 wherein said molecular composition is a function of boiling point.

58. The method of claim 49 wherein said molecular composition is aromatic ring distribution.

59. The method of claim 58 wherein said molecular composition is a function of boiling point.

60. The method of claim 41 wherein said process unit is a catalytic cracking unit.

61. The method of claim 41 wherein said process unit is a lube extraction unit.

62. The method of claim 61 wherein said material is a waxy distillate feed.

63. The method of claim 61 wherein said subfraction is the raffinate produced by extraction.

64. The method of claim 61 wherein said assay property is the raffinate yield.

65. The method of claim 61 wherein said assay property is raffinate viscosity.

66. The method of claim 61 wherein said assay property is raffinate viscosity index.

67. The method of claim 61 wherein said assay property is raffinate saturates content.

68. The method of claim 61 wherein said subfraction is the dewaxed raffinate produced by extraction and dewaxing.

69. The method of claim 61 wherein said assay property is the dewaxed raffinate yield.

70. The method of claim 61 wherein said assay property is dewaxed raffinate viscosity.

71. The method of claim 61 wherein said assay property is dewaxed raffinate viscosity index.

72. The method of claim 61 wherein said assay property is dewaxed raffinate saturates content.

* * * * *